(12) United States Patent
Choi et al.

(10) Patent No.: US 11,083,767 B2
(45) Date of Patent: Aug. 10, 2021

(54) PHARMACEUTICAL COMPOSITION COMPRISING AN EXTRACT OF PLATYCODON GRANDIFLORUM AND METHOD FOR PREVENTING OR TREATING OF OBESITY USING THE SAME

(71) Applicant: KYUNGPOOK NATIONAL UNIVERSITY INDUSTRY-ACADEMIC COOPERATION FOUNDATION, Daegu (KR)

(72) Inventors: Myung-Sook Choi, Daegu (KR); Eun-Young Kwon, Goyang-si (KR); Ye Jin Kim, Daegu (KR); Ri Ryu, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 781 days.

(21) Appl. No.: 15/603,624

(22) Filed: May 24, 2017

(65) Prior Publication Data
US 2018/0339007 A1    Nov. 29, 2018

(51) Int. Cl.
*A61K 36/346* (2006.01)
*A23L 33/105* (2016.01)
*A23L 33/00* (2016.01)

(52) U.S. Cl.
CPC .......... *A61K 36/346* (2013.01); *A23L 33/105* (2016.08); *A23L 33/30* (2016.08); *A23V 2002/00* (2013.01); *A61K 2236/33* (2013.01)

(58) Field of Classification Search
None
See application file for complete search history.

(56) References Cited

FOREIGN PATENT DOCUMENTS

KR    10-1685876 B1    12/2016

OTHER PUBLICATIONS

Kim, et al., J. Agric. Food Chem., 63:7721. (Year: 2015).*
Ahn, et al. Journal of Pharmacy and Pharmacoogy, 64:697. (Year: 2012).*
Hwang, et al., Toxicology and Pharmacology, 267:174. (Year: 2013).*
Byun, B-H., Korean Journal of Life Science, 13:896. (Year: 2003).*
Zhao, et al., Journal of Food Science, 73:H 195. (Year: 2008).*
Kim, et al., Nutrients, 8:532, including Supplementary Materials. (Year: 2016).*
Kim et al., "Supplementation of ethanol extract of platycodon grandiflorum root suppress body weight gain and body fat mass in diet-induced obese mice and ameliorates inflammation and insulin resistance", International Conference on Obesity & Chronic Diseases (ICOCD) / Poster Presentations, three pages, Jul. 25, 2016.
Kim et al., "Platycodon grandiflorus Root Extract Attenuates Body Fat Mass, Hepatic Steatosis and Insulin Resistance through the Interplay between the Liver and Adipose Tissue", Nutrients, ten pages, Aug. 30, 2016.

* cited by examiner

*Primary Examiner* — Michael Barker
(74) *Attorney, Agent, or Firm* — Vorys, Sater, Seymour & Pease LLP; Mih Suhn Koh

(57) ABSTRACT

Provided is a composition for preventing, improving or treating obesity, which includes a *Platycodon grandiflorum* extract as an active ingredient and a method for preparing the extract with an improved anti-obesity effect. The extract shows an effect of inhibiting increases in body weight and fat mass caused by a high-fat diet for normalization, an increase in fasting blood glucose and a decrease in energy expenditure in a diet-induced obesity mouse model. Further, compared to an extract prepared by a conventional extraction method, the *Platycodon grandiflorum* extract shows a more excellent effect of inhibiting increases in body weight and fat mass, fasting blood glucose, and blood lipid and adipokine contents in experiments, resulting in an excellent anti-obesity effect. Therefore, the *Platycodon grandiflorum* extract prepared is expected to be useful for preventing obesity and treating obesity-related complications that can be caused by an increase in fat mass as well as obesity.

9 Claims, 16 Drawing Sheets

PHARMACEUTICAL COMPOSITION COMPRISING AN EXTRACT OF PLATYCODON GRANDIFLORUM AND METHOD FOR PREVENTING OR TREATING OF OBESITY USING THE SAME

BACKGROUND

1. Field of the Invention

The present invention relates to a composition comprising a *Platycodon grandiflorum* extract as an active ingredient to prevent, improve or treat obesity, and a method for preparing a *Platycodon grandiflorum* extract with an improved anti-obesity effect.

2. Discussion of Related Art

Obesity is defined as excessive accumulation of fat tissue in the body, and occurs when the amount of intake calories is higher than the amount of calories consumed due to various causes such as mental and social factors, genetics, diseases and drugs. In 2010, according to the World Health Organization (WHO), it was estimated that the worldwide population of overweight adults was approximately 1.6 billion and the worldwide obesity population was approximately 400 million, and also reported that 2.6 million people die of obesity and excessive weight every year. In Korea, according to the reports by the Ministry of Health and Welfare and the Korea Centers for Disease Control and Prevention, the adult obesity rate was continuously increasing to 30.8% (male: 36.3%, female: 24.8%), based on 2010. As such, the obesity population is growing globally, and there is also a trend of growing medical expenses.

The awareness of the severity of obesity is greatly increasing because of the various complications that can be caused thereby, rather than its own risk. Obesity has been known to increase the risk factors of metabolic syndrome such as high blood pressure, hyperlipidemia and diabetes, fatty liver syndrome, dysarthrosis, and cancer. According to a WHO report in 2010, compared to people with normal body weights, people with obesity had a 2-fold or higher risk of high blood pressure, diabetes and dyslipidemia (2.5 fold for high blood pressure, 2 fold for diabetes, 2.3 fold for hypercholesterolemia, 2.4 fold for hypertriglyceridemia). In addition to the above-mentioned diseases, for women, due to the imbalance of sex hormones caused by excessive body fat, infertility may be caused, and it has been known that risks of endometrial cancer and breast cancer increase. In addition, since obesity may cause mental diseases such as social isolation or alienation, a lack of confidence, and depression as well as physical diseases, the necessity for preventing and treating obesity is considered very important.

Obesity may be treated by the improvement of lifestyle such as dietary therapy and behavior therapy as well as regular exercise, and drugs such as anorexics and fat absorption inhibitors. Since obesity is a chronic disease, drug treatment takes a long time, and as products currently approved for long-term use such as three months or longer in Korea, there are sibutramine as an anorexic, and orlistat as a lipase inhibitor. However, since such drugs for treating obesity are mostly psychotropic drugs for controlling appetite by acting on the central nervous system, they are accompanied by side effects such as headaches and nausea, and there are concerns about abuse. Therefore, studies have been actively conducted to develop a substance having high stability and an excellent anti-obesity effect, which can solve the side effects of commercially available anti-obesity agents.

Meanwhile, *Platycodon grandiflorum*, which is commonly known as the balloon flower and also called *Platycodon grandiflorum* root, is an oriental medical herb prepared by removing the root or periderm of *Campanula punctata* and the balloon flower, and known to have slight smell and bitter and spicy tastes, and to be mild-tempered. *Platycodon grandiflorum* acts on the lungs to treat symptoms such as asthma, excessive sputum and difficult breathing, stops coughing and removes sputum. In addition, *Platycodon grandiflorum* is also used when there is anasarca and a low amount of urine due to urinating difficulty. Therefore, *Platycodon grandiflorum* is used to treat sore throats, cold coughs, sputum, nasal congestion, asthma, bronchial inflammation, pleurisy, headaches, chills, tonsillitis, etc. As pharmacological actions, the removal of sputum, a decrease in cholesterol, and suppression of scabies bacteria (疥癬菌) have been reported.

Conventionally, *Platycodon grandiflorum* has been studied as a medical herb for preventing or treating obesity, and did not show a significant anti-obesity effect at a normal group level as a result of the experiments using various obesity animal models when a *Platycodon grandiflorum* extract was extracted. Therefore, the inventors confirmed an effect of normalizing body weight and fat mass due to the intake of the *Platycodon grandiflorum* extract, and thus completed the present invention.

SUMMARY OF THE INVENTION

Diet-induced obesity (DIO) mouse model was fed a *Platycodon grandiflorum* extract in combination with a high-fat diet, and then observed for 12 weeks. As a result, compared to a high-fat diet group, the DIO mouse showed almost similar body weight and fat mass levels to those of a normal diet group, and similar fasting blood glucose levels and energy expenditures to those of the normal diet group. It was confirmed that, compared to the *Platycodon grandiflorum* extract prepared by a conventional extraction method, the *Platycodon grandiflorum* extract according to the present invention exhibited a significantly improved anti-obesity effect, and thus the present invention was completed.

Therefore, the present invention is directed to providing a composition for preventing, improving or treating obesity, which comprises a *Platycodon grandiflorum* extract as an active ingredient to normalize body weight and fat mass.

The present invention is also directed to providing a method for preparing a *Platycodon grandiflorum* extract with an improved anti-obesity effect.

However, technical problems to be solved in the present invention are not limited to the above-described problems, and other problems which are not described herein will be fully understood by those of ordinary skill in the art from the following descriptions.

In one aspect, the present invention provides a pharmaceutical composition for preventing or treating obesity, which comprises a *Platycodon grandiflorum* extract as an active ingredient to normalize body weight and fat mass.

In another aspect, the present invention provides a health functional food composition for improving obesity, which comprises a *Platycodon grandiflorum* extract as an active ingredient to normalize body weight and fat mass.

In an exemplary embodiment of the present invention, the *Platycodon grandiflorum* extract may be extracted with a solvent selected from the group consisting of water, $C_1$ to $C_4$ lower alcohols, n-hexane, ethylacetate, acetone, butylacetate, 1,3-butylene glycol, methylene chloride, and a mixture thereof.

In another exemplary embodiment of the present invention, the *Platycodon grandiflorum* extract may be extracted with an ethanol solvent.

In still another exemplary embodiment of the present invention, the composition may inhibit increases in body weight and fat mass.

In yet another exemplary embodiment of the present invention, the composition may inhibit an increase in blood glucose.

In yet another exemplary embodiment of the present invention, the composition may inhibit a decrease in energy expenditure.

In yet another exemplary embodiment of the present invention, the composition may inhibit an increase in blood lipid contents.

In yet another exemplary embodiment of the present invention, the composition may inhibit an increase in blood adipokine contents.

In yet another exemplary embodiment of the present invention, the *Platycodon grandiflorum* extract may be contained at 3 to 10 wt % with respect to the total weight of the composition.

In still another aspect, the present invention provides a method for preventing or treating obesity, which includes administering the composition to a subject.

In yet another aspect, the present invention provides a use of the composition for preventing or treating obesity.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
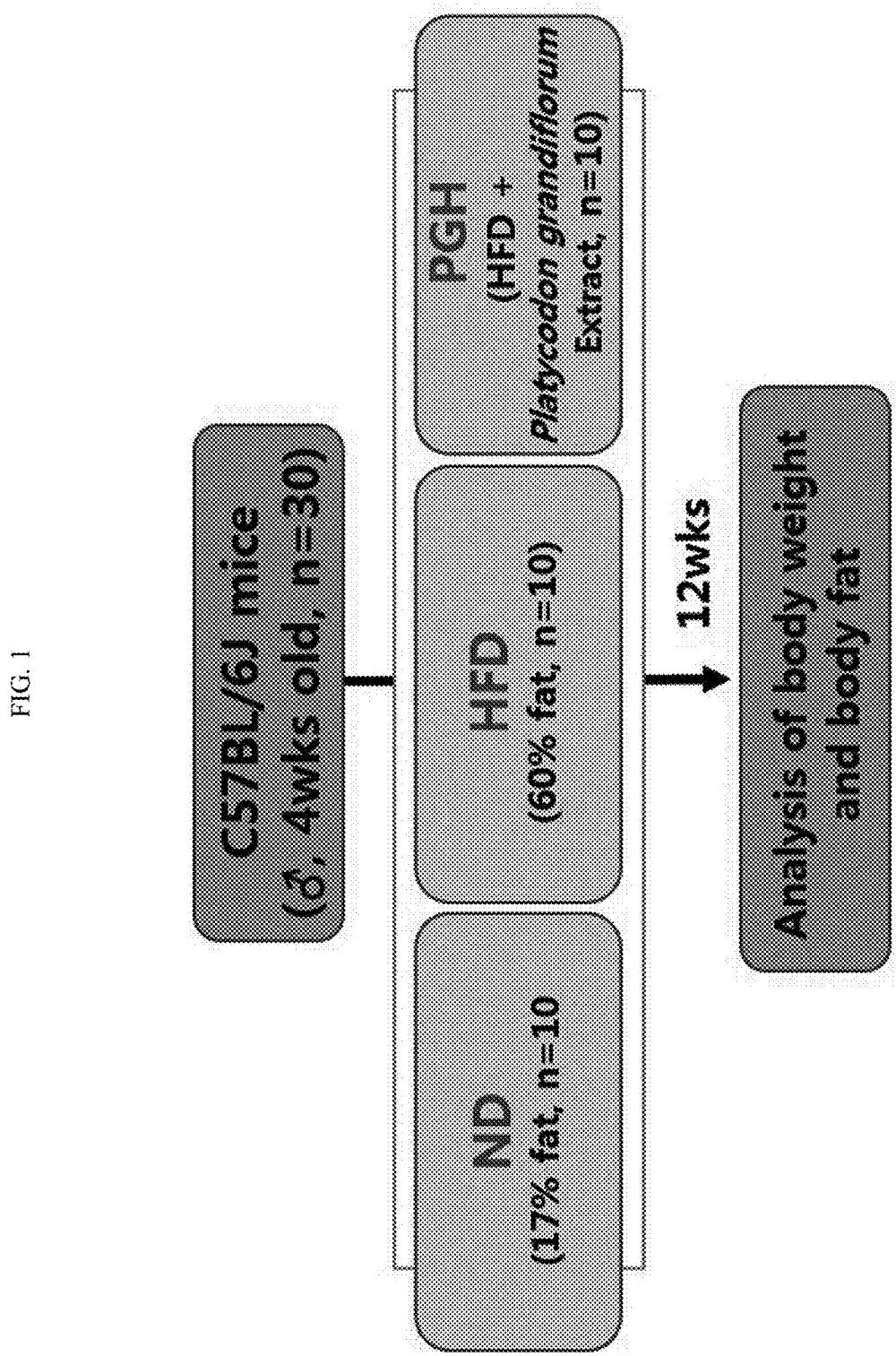
FIG. 1 is a schematic diagram of an experimental design using a DIO mouse model to evaluate the anti-obesity effect of a *Platycodon grandiflorum* extract.

The inventors observed an excellent anti-obesity effect of a *Platycodon grandiflorum* extract which was fed to a DIO mouse model in combination with a high-fat diet, and thus completed the present invention.

Therefore, the present invention provides a pharmaceutical composition for preventing or treating obesity, which comprises a *Platycodon grandiflorum* extract as an active ingredient to normalize body weight and fat mass.

In addition, the present invention provides a composition for reducing a body weight or fat mass, which comprises a *Platycodon grandiflorum* extract as an active ingredient.

The "obesity", a disease to be prevented or treated in the present invention, refers to excessive fat accumulation caused by proliferation and differentiation of adipocyte in a living organism due to metabolic disorders, and may cause related complications including metabolic syndrome accompanied by high blood pressure, diabetes and dyslipidemia. When energy uptake is increased relative to energy consumption, the number and volume of adipocytes are increased, and thus the mass of the adipose tissue is increased.

The term "prevention" used herein refers to all actions of inhibiting or delaying obesity by administration of the pharmaceutical composition according to the present invention.

The term "treatment" used herein refers to all actions involved in alleviating or beneficially changing symptoms of obesity by administration of the pharmaceutical composition according to the present invention.

The term "body fat" used herein refers to adipose tissue constituting a body, widely distributed in subcutaneous tissue, mammary glands, perirenal tissue, etc., and having functions of protecting internal organs and controlling body temperature in addition to serving as depot fat used as energy. Excessive accumulation of depot fat is called obesity, and for obesity, a body fat level is more significant than a body weight in terms of the prevention of obesity complications. It has been known that accumulation of visceral fat in the abdominal cavity, rather than subcutaneous fat, is highly related to saccharide and lipid metabolic disorders, high blood pressure, and coronary diseases. In the present invention, body fat includes both subcutaneous fat and visceral fat.

The present invention also provides a method for preparing a *Platycodon grandiflorum* extract with an improved anti-obesity effect, which includes the following steps:

(a) extracting *Platycodon grandiflorum* by the addition of an extraction solvent at 30 to 70° C.; and (b) concentrating the resulting extract under reduced pressure, followed by lyophilization.

The *Platycodon grandiflorum* extract may be extracted using one or more solvents selected from the group consisting of water, $C_1$ to $C_4$ alcohols, n-hexane, ethylacetate, acetone, butylacetate, 1,3-butylene glycol, methylene chloride, and a mixture thereof, preferably ethanol, and more preferably, 70% ethanol.

In Step (a), the extraction may be performed for 4 to 8 hours, and preferably 5 to 7 hours.

In Step (b), the concentration under reduced pressure may be performed at 40 to 60° C., and preferably 50° C.

The solvent may be removed by filtering, concentrating or drying the extract prepared as described above, or by all of filtration, concentration and drying thereof. For example, the filtration may be performed using filter paper or a vacuum filter, the concentration may be performed using a rotary evaporator, and the drying may be performed by lyophilization. However, the present invention is not limited thereto.

In addition, the extract obtained with the solvent may be further subjected to fractionation using a solvent selected from the group consisting of butanol, n-hexane, methylene chloride, acetone, ethylacetate, ethylether, chloroform, water and a mixture thereof. During fractionation, a temperature may be 4 to 120° C., but the present invention is not limited thereto.

In an exemplary embodiment of the present invention, to evaluate the anti-obesity effect of the *Platycodon grandiflorum* extract prepared by the above-described method, experiments are carried out using DIO mouse model.

In an exemplary embodiment of the present invention, male C57BL/6J mice were divided into a normal diet group, a high-fat diet group, and a *Platycodon grandiflorum* extract-fed group and fed for 12 weeks, followed by measurement of body weights. As a result, it was observed that, in the high-fat diet group, compared to the normal diet group, body weights were rapidly increased, but in the *Platycodon grandiflorum* extract-fed group, body weights were increased to a level similar to the normal diet group. Therefore, it was confirmed that the *Platycodon grandiflorum* extract is effective in normalizing body weight (see Example 2-1).

In addition, mice of each group were fed for 12 weeks by the same method as described above and then sacrificed to collect liver, kidney, muscle, as well as visceral fat and subcutaneous fat from various sites, followed by measurement of weights. As a result, it was confirmed that, in the high-fat diet group, the liver weight was increased and the kidney and muscle weights were decreased, but in the *Platycodon grandiflorum* extract-fed group, weights similar to those of the normal diet group (see Example 2-2). As a result of measuring the weights of visceral fat and subcutaneous fat in different sites, it was confirmed that the *Platycodon grandiflorum* extract-fed group shows weights of total adipose tissue similar to those of the normal diet group, and the *Platycodon grandiflorum* extract is effective in normalizing fat mass (see Example 2-3).

In another exemplary embodiment of the present invention, as a result of measuring fasting blood glucose every two weeks during the 12-week feeding duration for the respective mouse groups, it was confirmed that the *Platycodon grandiflorum* extract-fed group showed low fasting blood glucose levels similar to those of the normal diet group (see Example 3), and as a result of comparing energy expenditures between the groups for 24 hours, it was confirmed that the high-fat diet group shows a significantly low energy expenditure, and the *Platycodon grandiflorum* extract-fed group shows an energy expenditure pattern similar to that of the normal diet group (see Example 4).

Therefore, according to the results obtained in the examples of the present invention, it can be seen that the *Platycodon grandiflorum* extract has a normalizing effect of body weight and fat mass.

In addition, in exemplary embodiments of the present invention, it was confirmed that the *Platycodon grandiflo-*

*rum* extract according to the present invention has an excellent anti-obesity effect, compared to that prepared by a conventional extraction method.

In an exemplary embodiment of the present invention, mice were divided into a normal diet group, a high-fat diet group, a *Platycodon grandiflorum* extract prepared by a conventional extraction method-fed group, and an *Platycodon grandiflorum* extract according to the present invention-fed group, and fed for 12 weeks, followed by measurement of changes in body weight, and thus it was confirmed that the *Platycodon grandiflorum* extract according to the present invention has a further excellent effect of inhibiting an increase in body weight (see Example 5-2). And after the 12-week feeding, the liver, kidney, total muscle, and various types of white adipose tissue were isolated from the mice in the different groups to measure weights. According to comparative results, it was confirmed that the *Platycodon grandiflorum* extract according to the present invention has a more excellent effect of inhibiting an increase in liver weight, and decreases in kidney and muscle weights (see Example 5-3), and also has the effect of inhibiting an increase in fat mass to the normal group level, and thus has an excellent anti-obesity effect (see Example 5-4).

In another exemplary embodiment of the present invention, according to comparative analysis on effects of the *Platycodon grandiflorum* extract according to the present invention and the *Platycodon grandiflorum* extract prepared by a conventional extraction method on blood lipid contents, fasting blood glucose and insulin resistance, and blood adipokine levels, it was confirmed that the *Platycodon grandiflorum* extract according to the present invention has a more excellent effect (see Examples 6 and 7).

Therefore, the *Platycodon grandiflorum* extract according to the present invention with an excellent anti-obesity effect may be contained at 3 to 10 wt %, and preferably, 5 wt % with respect to the total weight of the composition, but the present invention is not limited thereto.

The pharmaceutical composition according to the present invention includes the *Platycodon grandiflorum* extract as an active ingredient, and may further include a pharmaceutically acceptable carrier. The pharmaceutically acceptable carrier is conventionally used for preparation, and may be, but is not limited to, a saline solution, distilled water, Ringer's solution, buffered saline, a cyclodextrin solution, a dextrose solution, a maltodextrin solution, glycerol, ethanol, or liposomes, etc., and may further include another conventional additive such as an antioxidant or a buffer as needed. In addition, the pharmaceutically acceptable carrier may be prepared as injectable forms such as an aqueous solution, a suspension, and an emulsion, pills, capsules, granules or tablets by further adding diluents, dispersants, surfactants, binders, lubricants, etc. Suitable pharmaceutically acceptable carriers and their preparations may be prepared according to each component using a method disclosed in the Remington's Pharmaceutical Science. The pharmaceutical composition of the present invention is not limited to dosage forms, and thus may be prepared as injections, inhalants, or topical formulations for skin.

The pharmaceutical composition of the present invention may be administered orally or parenterally (e.g., intravenously, subcutaneously, intraperitoneally, or topically) according to a desired method, and a dose of the pharmaceutical composition of the present invention may be selected according to a patient's condition and body weight, severity of a disease, a dosage form, an administration route and duration by those of ordinary skill in the art.

The pharmaceutical composition of the present invention is administered at a pharmaceutically effective amount. In the present invention, the "pharmaceutically effective amount" refers to an amount sufficient to treat the disease at a reasonable benefit/risk ratio applicable for medical treatment, and an effective dosage may be determined by parameters including a type of a patient's disease, severity, drug activity, sensitivity to a drug, administration time, an administration route and an excretion rate, the duration of treatment and drugs simultaneously used, and other parameters well known in the medical field. The pharmaceutical composition of the present invention may be administered separately or in combination with other therapeutic agents, and may be sequentially or simultaneously administered with a conventional therapeutic agent, or administered in a single dose or multiple doses. In consideration of all of the above-mentioned parameters, it is important to achieve the maximum effect with the minimum dose without a side effect, and such a dose may be easily determined by one of ordinary skill in the art.

Specifically, the effective amount of the compound according to the present invention may vary depending on a patient's age, sex, condition and body weight, an absorption rate of the active ingredient in the body, an inactivation rate, an excretion rate, a type of disease, or a drug used in combination, and may be generally administered at 0.001 to 150 mg and, preferably, 0.01 to 100 mg/kg of body weight daily or every other day, or once to three times a day. However, the effective amount may vary depending on an administration route, the severity of obesity, sex, body weight or age, and therefore, the scope of the present invention is not limited by the dose by any means.

In addition, the present invention provides a health functional food composition for improving obesity, which comprises the *Platycodon grandiflorum* extract of the present invention as an active ingredient to normalize body weight and fat mass.

The term "improvement" used herein refers to all types of actions that at least reduce parameters related to a condition to be treated, for example, a degree of a symptom. Here, the health functional food composition may be simultaneously or separately used with a therapeutic agent before or after the onset of a corresponding disease to prevent or improve obesity.

The term "health functional food composition" used herein is formulated as one selected from the group consisting of tablets, pills, powder, granules, capsules or liquids, which contain one or more of carriers, diluents, dispersants and additives. Examples of foods that can be added to the extract of the present invention include various types of foods, powder, granules, tablets, capsules, syrup, drinks, gum, tea, vitamin complexes, and health functional foods. As an additive that can be further contained in the present invention, one or more components may be selected from the group consisting of natural carbohydrates, seasonings, nutrients, vitamins, minerals (electrolytes), flavoring agents (synthetic flavoring agents, natural flavoring agents, etc.), coloring agents, fillers, pectic acid and a salt thereof, alginic acid and a salt thereof, organic acids, protective colloidal thickening agents, pH adjustors, stabilizers, preservatives, antioxidants, glycerin, alcohol, carbonizing agents, and fruit flesh. Examples of the natural carbohydrates include conventional saccharides, for example, monosaccharides such as glucose, fructose, etc.; disaccharides such as maltose, sucrose, etc.; and polysaccharides such as dextrin, cyclodextrin, etc., and sugar alcohols such as xylitol, sorbitol, erythritol, etc. As the flavoring agents, natural flavoring agents (thaumatin and stevia extracts (e.g., rebaudioside A, glycyrrhizin, etc.)) and artificial flavoring agents (saccharin, aspartame, etc.) may be beneficially used. In addition to these components, the composition according to the present invention may contain various types of nutrients, vitamins, minerals (electrolytes), flavors such as synthetic flavors and natural flavors, coloring agents and thickening agents, pectic acid and a salt thereof, alginic acid and a salt thereof, organic acids, protective colloidal thickening agents, pH adjustors, stabilizers, preservatives, glycerin, alcohol, a carbonating agent used for soft drinks. In addition, another composition according to the present invention may contain flesh for preparing a natural fruit juice and a vegetable drink. Such components may be used independently or in combination. Specific examples of a carrier, excipient, diluent or additive may be, but are not limited to, one or more selected from the group consisting of lactose, dextrose, sucrose, sorbitol, mannitol, erythritol, starch, acasia gum, calcium phosphate, alginate, gelatin, calcium phosphate, calcium silicate, microcrystalline cellulose, polyvinylpyrrolidone, cellulose, methyl cellulose, water, sugar syrup, methylhydroxybenzoate, propylhydroxybenzoate, talc, magnesium stearate, and mineral oil.

In addition, the present invention provides a method for preventing or treating obesity, which includes administering the pharmaceutical composition to a subject.

The "subject" used herein refers to a target with a disease in need of treatment, specifically, including a mammal such as a human or a non-human primate, a mouse, a dog, a cat, a horse, or a cow.

Hereinafter, exemplary examples will be provided to help in understanding of the present invention. However, the following examples are merely provided to facilitate understanding of the present invention, and the scope of the present invention is not limited to the following examples.

EXAMPLES

Example 1. Preparation of *Platycodon grandiflorum* Extract and Analysis of Active Ingredient

*Platycodon grandiflorum* was obtained from Omniherb, Korea, grinded to facilitate extraction, and extracted with 30 L of 70% ethanol per 3 kg of the *Platycodon grandiflorum* for 6 hours at 50° C. The extraction was performed once, and the extract was concentrated under reduced pressure at 50° C. and then lyophilized for use in the experiments. The *Platycodon grandiflorum* extract was obtained with a yield of 13.3%.

To analyze an active ingredient of the *Platycodon grandiflorum* extract obtained by the above-described method, HPLC and MS analyses were performed, and analysis conditions are shown in Table 1.

TABLE 1

| HPLC Operating condition | |
|---|---|
| Model | Shimadzu LC |
| Column | Kinetex C18 column (100 × 2.1 mm, 2.6 μm, Phenomanex) |
| Run time | 35 min Flow rate 200 μL/min Inj, volume 5 μL |
| Solvent | A: 0.1% formic acid in water |
| | B: 0.1% formic acid in Acetonitrile |
| Gradient | B: 0 min (5%) → 2 min (5%) → 5 min (20%) → 10 min (20%) → 17 min (30%) → 30 min (30%) → 35 min (5%) |

| MS Operating condition | | | | | | |
|---|---|---|---|---|---|---|
| Model | Shimadzu LC MS-8040 (Triple Quadrupole Mass spectrometer) | | | | | |
| Spray Vol. | Vaporizer Temp. | Capillary Temp. | Sheath (Neb) Gas | Ion Sweep Gas | Aux Gas | Drying Gas |
| (+) 4000 V | 300° C. | 350° C. | 3 L/min | 2.0 Arb | 10 Arb | 8 L/min |

| Gas | | | |
|---|---|---|---|
| Neb/Dry/Aux gas | Nitrogen | Collision gas | Argon |
| MS/MS Charge | Collision energy Positive mode | 70 eV | CID gas pressure Pressure | 230 KPa 152 Bar |

As a result of the analyses, total 18 types of active ingredients were analyzed, and their names and contents are shown in Table 2.

TABLE 2

| No. | Saponin name | Content (μg/mg) | Content (%) |
|---|---|---|---|
| 1 | Deapioplatycoside E | 0.49 | 0.05 |
| 2 | Platycoside E | 0.56 | 0.06 |
| 3 | Deapioplatycodin D3 | 0.51 | 0.05 |
| 4 | Platycodin D3 | 1.87 | 0.19 |
| 5 | Platyconic acid B Lactone | 0.01 | 0.00 |
| 6 | Polygalacin D3 | 0.56 | 0.06 |
| 7 | Platycoinc acid A | 0.88 | 0.09 |
| 8 | 3"-O-acetylplatyconic acid A | 3.50 | 0.35 |
| 9 | Platycodin D2 | 1.84 | 0.18 |
| 10 | Platycodin D | 1.71 | 0.17 |
| 11 | 3"-O-acetylplatycodin D2 | 1.56 | 0.16 |
| 12 | Polygalacin D2 | 0.59 | 0.06 |
| 13 | Polygalacin D | 0.27 | 0.03 |
| 14 | 3"-O-acetylplatycodin D | 10.25 | 1.03 |
| 15 | Platycodin V | 1.61 | 0.16 |
| 16 | Platycodin A | 10.28 | 1.03 |

TABLE 2-continued

| No. | Saponin name | Content (µg/mg) | Content (%) |
|---|---|---|---|
| 17 | 2″-O-acetylpolygalacin D2 | 2.34 | 0.23 |
| 18 | 2″-O-acetylpolygalacin D | 1.28 | 0.13 |

Example 2. Analysis of Changes in Body Weight and Organ Weight Due to the *Platycodon grandiflorum* Extract 2-1. Analysis of Changes in Body Weight To examine the effect of the intake of the *Platycodon grandiflorum* extract on an increase in body weight in dietary DIO mouse model, experiments were designed and carried out as shown in the schematic diagram of FIG. 1. Specifically, 4-week-old male C57BL/6J mice (n=30) were obtained from the Jackson Laboratory, fed a lab chow diet for one-week acclimation, and divided into a normal diet group (ND), a high-fat diet group (HFD), and the *Platycodon grandiflorum* extract-fed group (PGH, 5% *Platycodon grandiflorum* extract+high-fat diet) with 10 mice each for 12-week feeding, and body weights were measured at one-week intervals.

Figure 2:
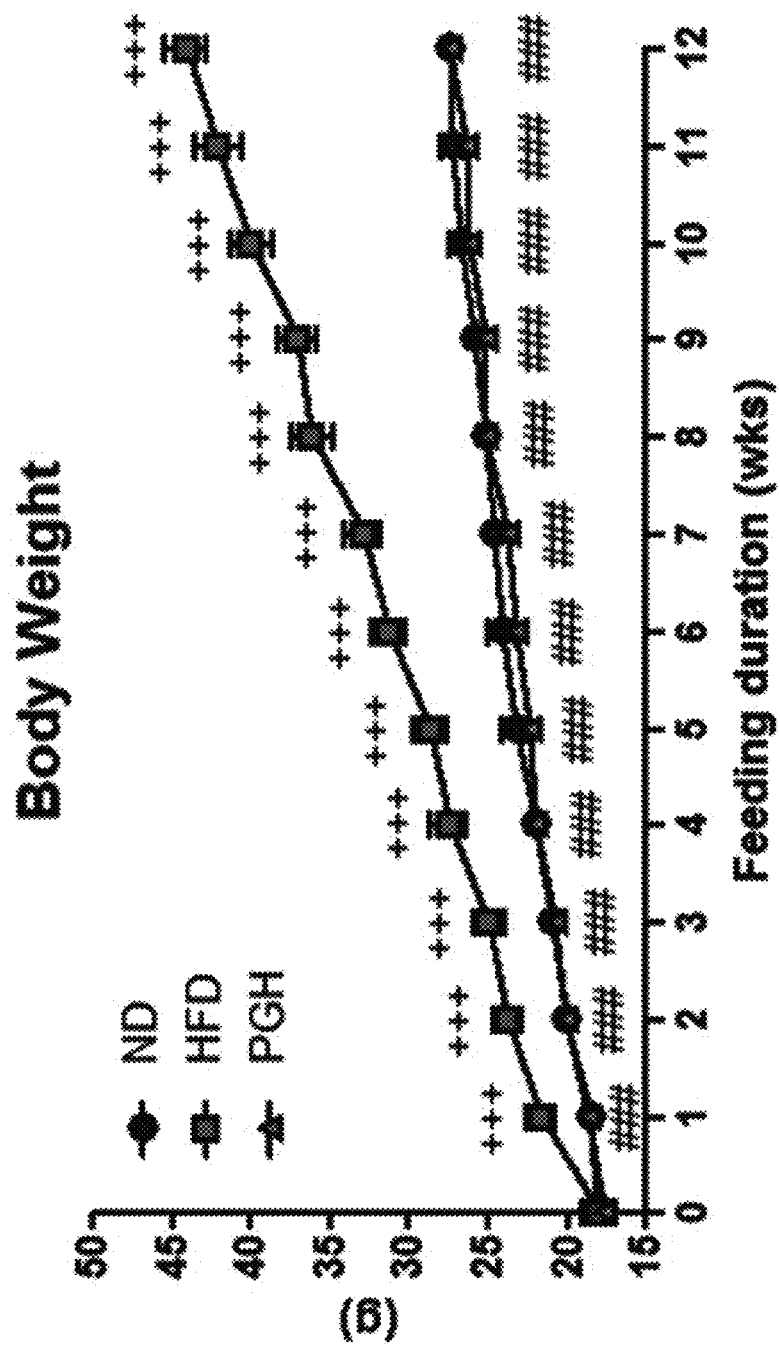
FIG. 2 shows body weight changes according to feeding duration by measuring body weights of mice in a normal diet group (ND), a high-fat diet group (HFD), and a *Platycodon grandiflorum* extract-fed group (PGH) every week for 12 weeks.

Consequently, as shown in FIG. 2, it was observed that the high-fat diet group (HFD) shows a drastic increase in body weight, compared to the normal diet group (ND), and the *Platycodon grandiflorum* extract-fed group (PGH) shows an increase in body weight to a level similar to that of the normal diet group (ND) after one-week feeding. In addition, as a result of the comparison of the respective groups by quantifying the results, as shown in Table 3, compared to the high-fat diet group (HFD), the *Platycodon grandiflorum* extract-fed group (PGH) had an almost similar daily food intake, but almost half of the increase in body weight, and therefore it was confirmed that the increase in body weight was inhibited due to the intake of the *Platycodon grandiflorum* extract. As a result, it can be seen that the *Platycodon grandiflorum* extract is effective in normalizing body weight.

TABLE 3

| | Initial Body weight(g) | Final Body weight(g) | Body weight gain(g) | Food intake(g/day) |
|---|---|---|---|---|
| ND | 18.19 ± 0.54 | 27.43 ± 0.49 | 10.26 ± 0.46 | 2.60 ± 0.06 |
| HFD | 18.81 ± 0.84 | 44.76 ± 1.38*** | 31.33 ± 4.16*** | 2.78 ± 0.05 |
| PGH | 17.67 ± 0.29 | 27.37 ± 0.28### | 14.55 ± 3.55### | 2.51 ± 0.11 |

2-2. Analysis of Organ Weight

In addition to the analysis of the changes in body weight in Example 2-1, it was intended to examine the effect of the intake of the *Platycodon grandiflorum* extract on organ weights in dietary DIO mouse model. To this end, after the 12-week feeding by the method of Example 2-1, the mice in each group fasted for 12 hours, were sacrificed after anesthetization through inhalation of isoflurane (Baxter, USA), and then subjected to organ extraction. The collected liver, kidney and muscle tissues of each mouse were washed with phosphate buffered saline (PBS) several times for dehydration, and then weights of these tissues were measured and expressed as weight per 100 g body weight for comparison.

Figure 3:
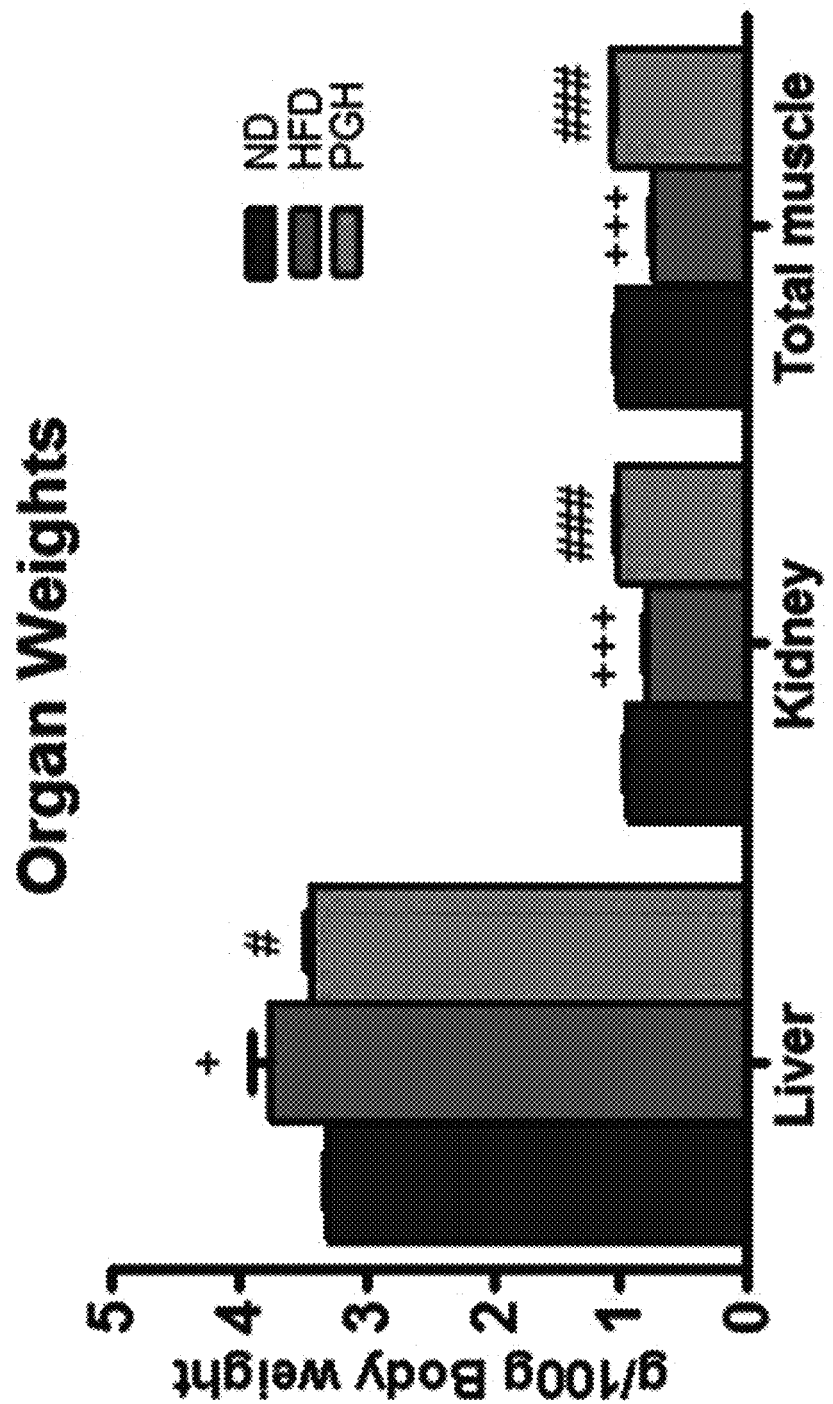
FIG. 3 shows weights of the liver, kidney and total muscle extracted from mice in a normal diet group (ND), a high-fat diet group (HFD), and a *Platycodon grandiflorum* extract-fed group (PGH), measured after 12 weeks of feeding and expressed as weight per 100 g body weight.

Consequently, as shown in FIG. 3, compared to the normal diet group (ND), the liver weight was significantly increased in the high-fat diet group (HFD), but significantly decreased in that of the *Platycodon grandiflorum* extract-fed group, compared to the high-fat diet group (HFD). Compared to the normal diet group, the kidney and muscle weights were significantly decreased in the high-fat diet group, but the *Platycodon grandiflorum* extract-fed group showed similar kidney and muscle weights. As a result, it can be seen that the *Platycodon grandiflorum* extract inhibits an increase in liver weight and a decrease in kidney and muscle weights.

2-3. Analysis of Weights of Adipose Tissue

To analysis of changes in the weight of adipose tissue due to the intake of the *Platycodon grandiflorum* extract, adipose tissue, that is, visceral white adipose tissue (visceral WAT) such as epididymal WAT, perirenal WAT, retroperitoneal WAT, mesenteric WAT and subcutaneous WAT, interscapular WAT, and interscapular brown adipose tissue (interscapular BAT) were collected from each mouse by the method described in Example 2-2, and weights of these tissue were measured and expressed as weight per 100 g body weight for comparison.

Figure 4A:
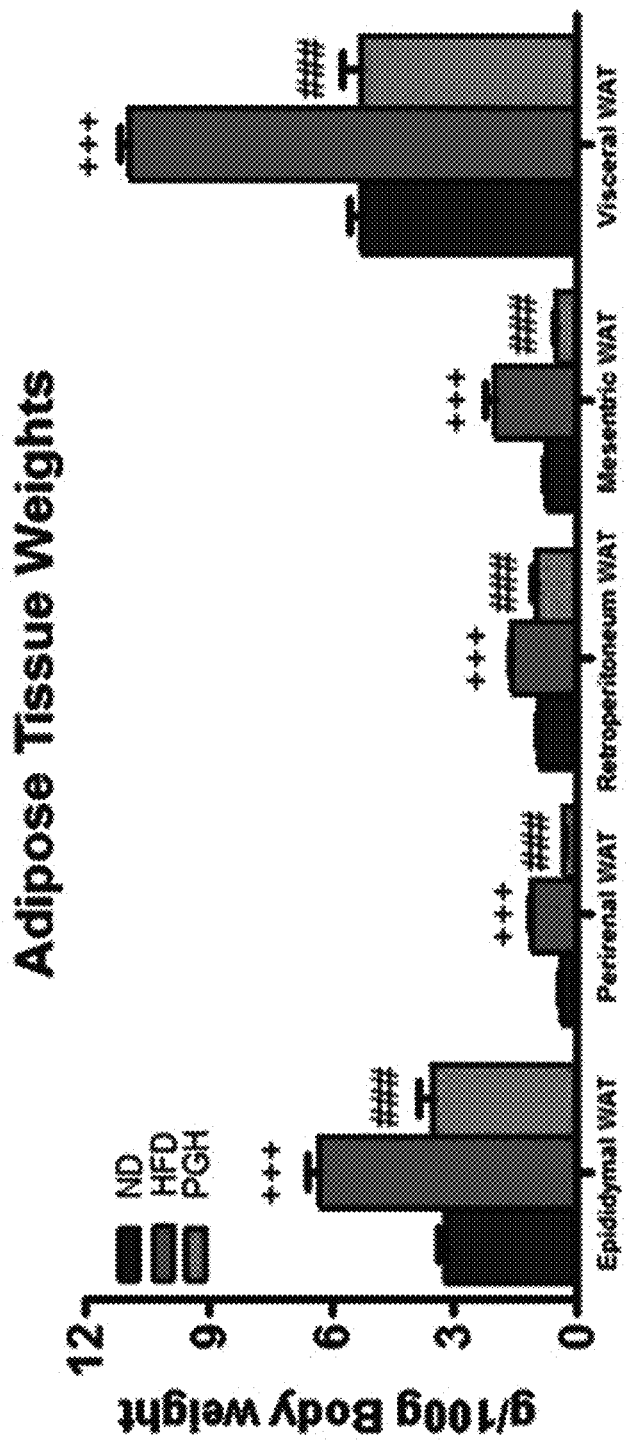
FIG. 4A shows weights of epididymal white adipose tissue (WAT), perirenal WAT, retroperitoneal WAT, mesenteric WAT, and visceral WAT extracted from mice in a normal diet group (ND), a high-fat diet group (HFD), and a *Platycodon grandiflorum* extract-fed group (PGH), measured after 12 weeks of feeding and expressed as weight per 100 g body weight.

Consequently, as shown in FIG. 4A, it was confirmed that, compared to the normal diet group (ND), all of the epididymal WAT, the perirenal WAT, the retroperitoneal WAT, the mesenteric WAT, and the total visceral WAT were considerably increased in weight in the high-fat diet group (HFD), but the *Platycodon grandiflorum* extract-fed group (PGH) showed similar weights.

Figure 4B:
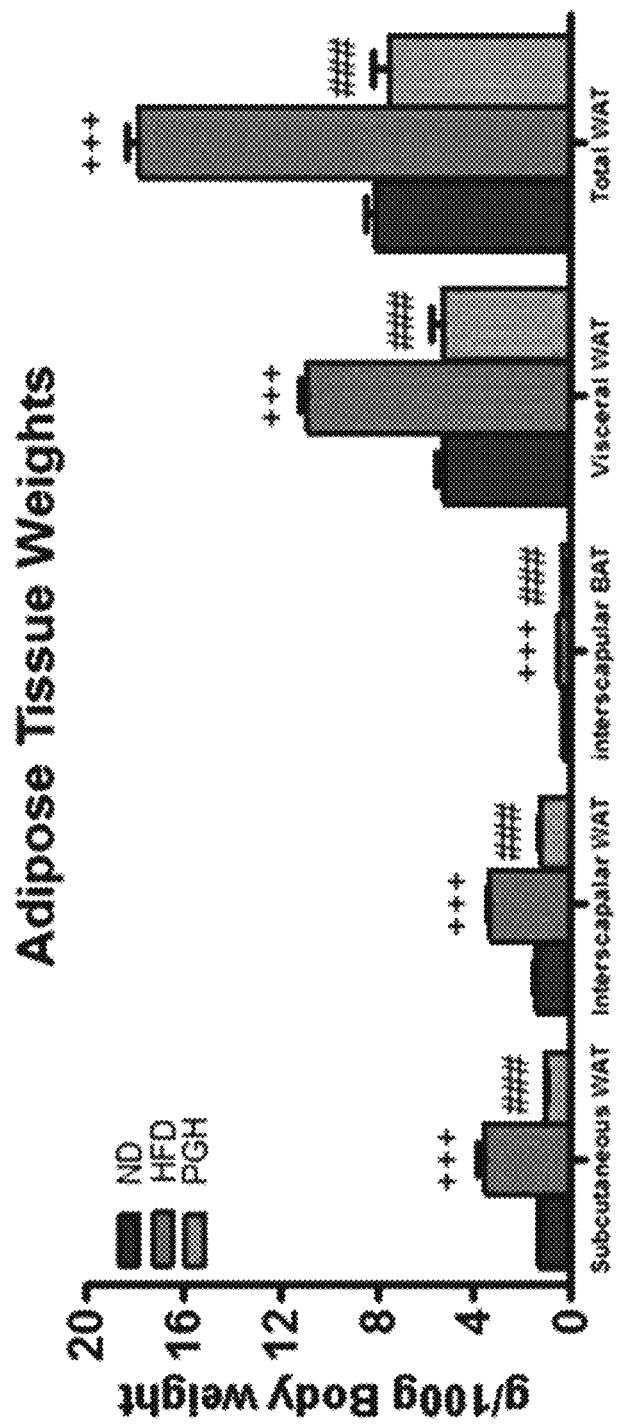
FIG. 4B shows weights of subcutaneous WAT, interscapular WAT, interscapular brown adipose tissue (BAT), visceral WAT, and total WAT extracted from mice in a normal diet group (ND), a high-fat diet group (HFD), and a *Platycodon grandiflorum* extract-fed group (PGH), measured after 12 weeks of feeding and expressed as weight per 100 g body weight.

In addition, by comparing the weights of the subcutaneous WAT, the interscapular WAT, the interscapular BAT, the total visceral WAT, and the total WAT, as shown in FIG. 4B, in the same manner as the analysis results of the visceral WAT weights in FIG. 4A, it was confirmed that, in the *Platycodon grandiflorum* extract-fed group, weights of the adipose tissue are similar to the normal diet group. As a result, it can be seen that the *Platycodon grandiflorum* extract significantly reduced the WAT level of each site of the body to a normal diet group level, indicative of the effect of normalizing WAT levels.

Example 3. Analysis of Effect of *Platycodon grandiflorum* Extract on Changes in Blood Glucose Form the results obtained in Example 2, it was confirmed that the intake of the *Platycodon grandiflorum* extract is effective in normalizing body weight and fat mass, and therefore, it was intended to examine whether the intake of the *Platycodon grandiflorum* extract has an influence on changes in blood glucose levels. To this end, mice fasted for 12 hours once every two weeks during the 12-week feeding duration according to the method described in Example 2-1, followed by collecting blood from a tail to measure fasting blood glucose.

Figure 5:
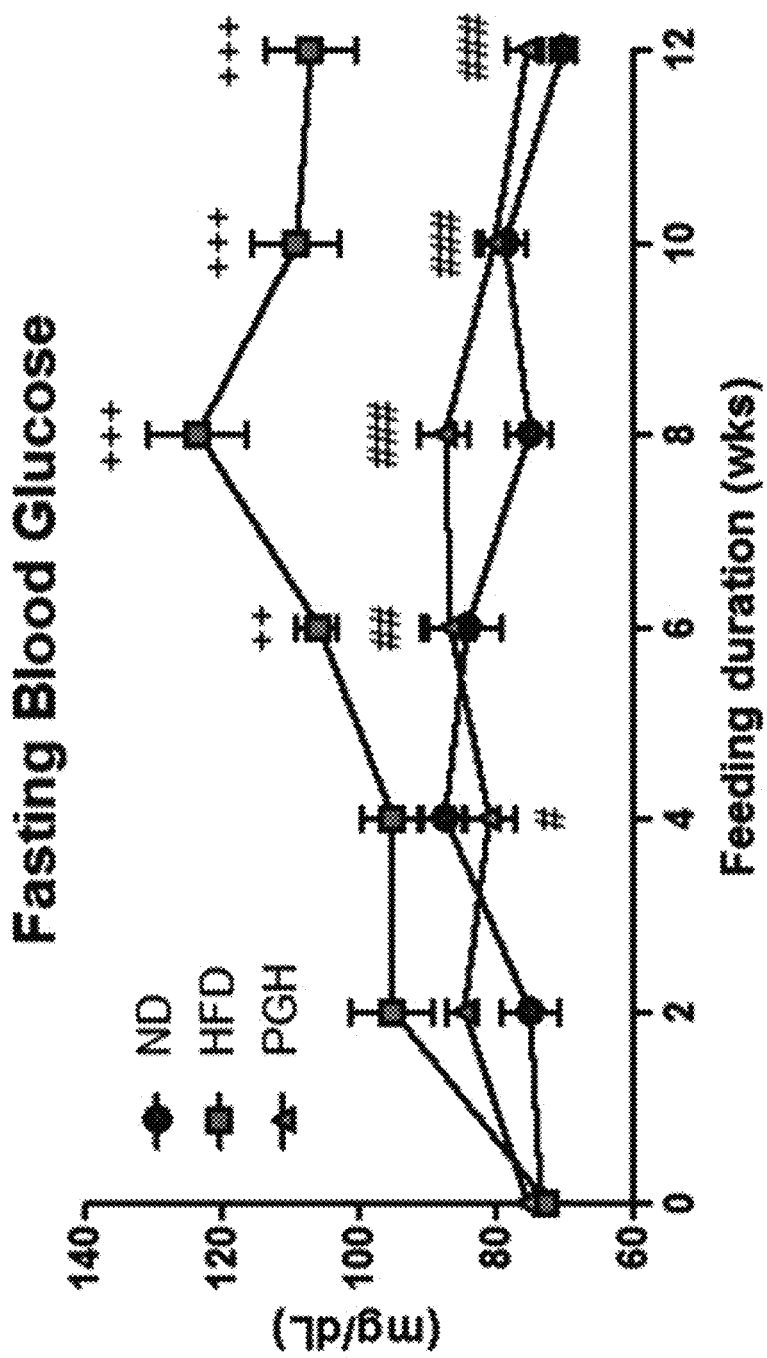
FIG. 5 shows changes in the blood glucose level according to feeding duration by measuring fasting blood glucose of mice in a normal diet group (ND), high-fat diet group (HFD), and a *Platycodon grandiflorum* extract-fed group (PGH) every two weeks for 12 weeks.

As a result, as shown in FIG. 5, the high-fat diet group (HFD) showed the maximum blood glucose level on the $8^{th}$ week of the feeding duration, and maintained significantly increased blood glucose levels from the $6^{th}$ week of the feeding duration, compared to the normal diet group (ND). Meanwhile, it was confirmed that the *Platycodon grandiflorum* extract-fed group (PGH) maintained blood glucose levels similar to those of the normal diet group throughout the feeding duration. Consequently, it can be seen that the *Platycodon grandiflorum* extract is highly effective in reducing blood glucose.

Example 4. Analysis of Effect of *Platycodon grandiflorum* Extract on Enemy Expenditure It was intended to examine whether the intake of the *Platycodon grandiflorum* extract is effective in normalizing body weight and fat mass, reducing blood glucose, and has an effect on energy expenditure (EE). To this end, in the 12-week feeding duration by the method of Example 2-1, energy expenditure of the mice was measured using a device for measuring an animal metabolic rate (Oxylet; Panlab, Cornelia, Spain). More specifically, after the calibration of the measuring device with oxygen and carbon, a flow rate in a cage was adjusted to 3 L/min. Afterward, each mouse was put into a separate metabolic cage to measure energy consumption (oxygen uptake) for 24 hours. The energy expenditure was derived by substituting and calculating according to Equation 1.

$$EE \text{ (kcal/day/body weight}^{0.75})=Vo_2\times1.44\times[3.815+(1.232\times Vo_2/Vco_2)] \quad \text{[Equation 1]}$$

Figure 6A:
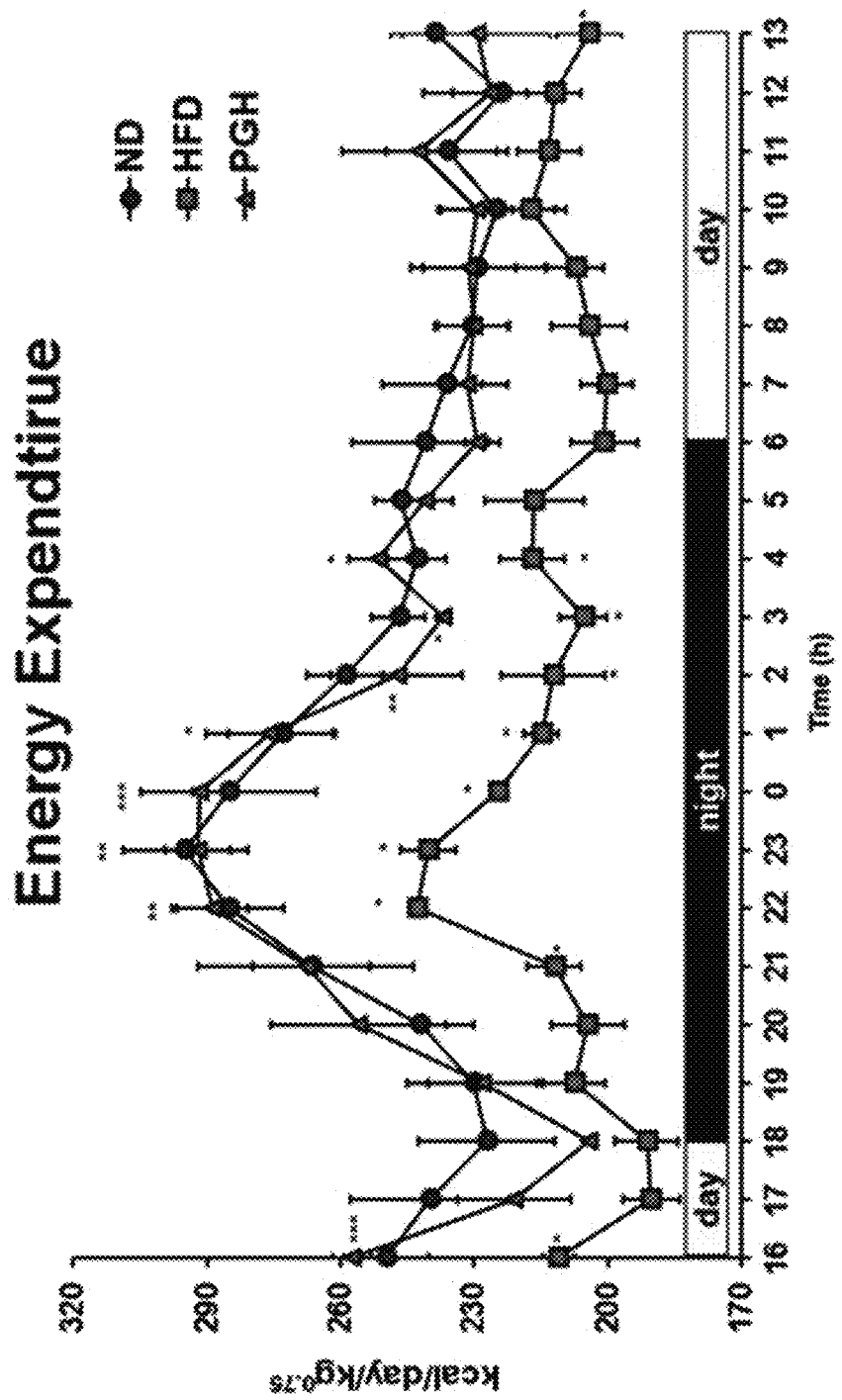
FIG. 6A shows changes in the energy expenditure over time by measuring energy consumption of mice in a normal diet group (ND), a high-fat diet group (HFD), and a *Platycodon grandiflorum* extract-fed group (PGH) for 24 hours using an animal metabolic rate measuring device.
Figure 6B:
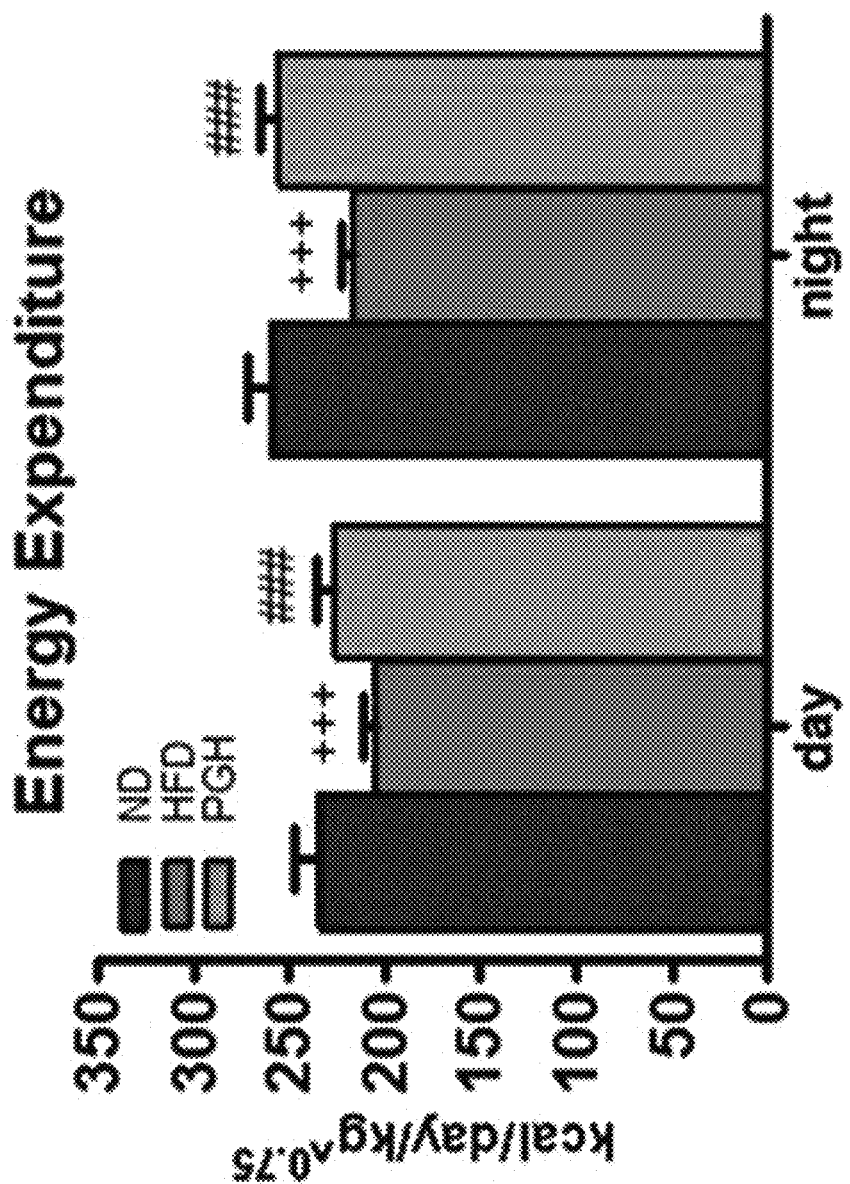
FIG. 6B shows energy expenditures of mice in a normal diet group (ND), a high-fat diet group (HFD), and a *Platycodon grandiflorum* extract-fed group (PGH), quantified with respect to day and night for 24 hours.

As a result, as shown in FIG. 6A, it was confirmed that the high-fat diet group (HFD) showed a significantly lower energy expenditure than the normal diet group (ND), but the *Platycodon grandiflorum* extract-fed group (PGH) showed an energy metabolic rate pattern similar to that of the normal diet group. Particularly, as shown in FIG. 6B, by quantitatively comparing energy metabolic rates by day and night, it can be seen that the *Platycodon grandiflorum* extract-fed group shows a higher energy metabolic rate at night than by day. Consequently, it can be seen that the *Platycodon grandiflorum* extract increased the energy metabolic rate.

Example 5. Comparative Analysis of Changes in Body Weight and Organ Weight Due to *Platycodon grandiflorum* Extract According to Extraction Method 5-1. Preparation of *Platycodon grandiflorum* Extract Since there has been no research result to confirm a significant anti-obesity effect of normalizing body weight and body fat using the *Platycodon grandiflorum* extract until now, the anti-obesity effect of the *Platycodon grandiflorum* extract of the present invention prepared by the method shown in Example 1 was comparatively analyzed with the effect of a *Platycodon grandiflorum* extract that was previously studied to examine whether the *Platycodon grandiflorum* extract of the present invention has a more excellent anti-obesity effect.

To this end, the *Platycodon grandiflorum* extract of the present invention (hereinafter, referred to as PGE2) was prepared by the method described in Example 1, to prepare the *Platycodon grandiflorum* extract prepared by a conventional method (hereinafter, referred to as PGE1), the same amounts of *Platycodon grandiflorum* and an extraction solvent as used in the present invention were used, but a different extraction method was used. More specifically, 30 L of 70% ethanol as an extraction solvent was applied to 3 kg of *Platycodon grandiflorum* to carry out extraction at room temperature for 24 hours. An extract obtained after repeating extraction twice was concentrated under reduced pressure at 40° C. and then lyophilized before use, and the yield of the extract was 20%.

5-2. Comparative Analysis of Changes in Body Weight

To compare the effect of each of the *Platycodon grandiflorum* extract of the present invention (PGE2) and the *Platycodon grandiflorum* extract (PGE1) prepared using a conventional extraction method on an increase in body weight, a change in the body weight were analyzed using a DIO mouse model.

Figure 7:
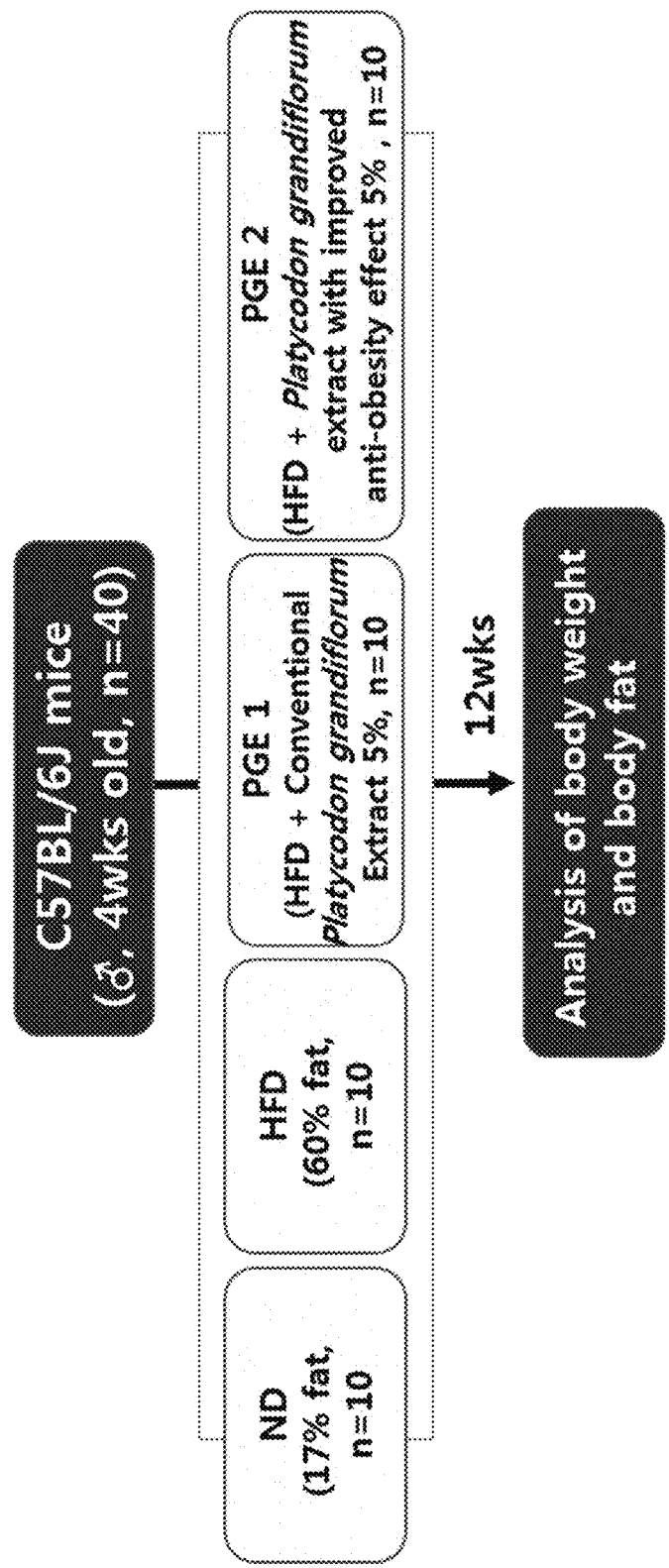
FIG. 7 is a schematic diagram of an experimental design using a DIO mouse model for comparative analysis of the anti-obesity effects of a *Platycodon grandiflorum* extract according to the present invention (PGE2) and a *Platycodon grandiflorum* extract prepared by a conventional extraction (PGE1) method.

More specifically, as shown in FIG. 7, 4-week-old male C57BL/6J mice (n=40) were purchased from the Jackson Laboratory, fed a lab chow diet for one-week acclimation and divided into a normal diet group (ND), a high-fat diet group (HFD), a *Platycodon grandiflorum* extract prepared by a conventional extraction method-fed group (PGE1, 5% *Platycodon grandiflorum* extract+high-fat diet), and a *Platycodon grandiflorum* extract of the present invention-fed group (PGE2, 5% *Platycodon grandiflorum* extract+high-fat diet) with 10 mice each for 12-week feeding, followed by measurement of their body weights.

Figure 8:
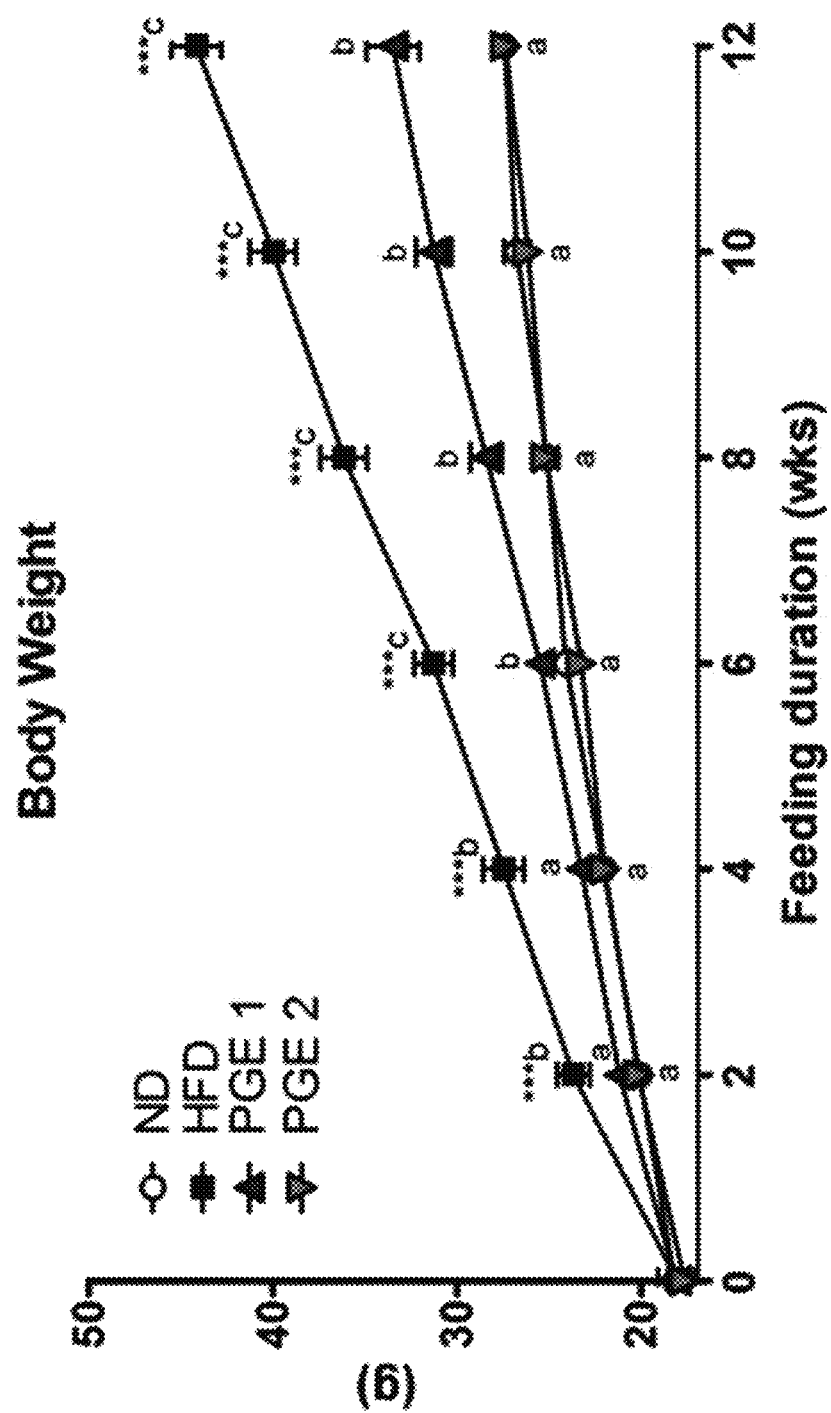
FIG. 8 shows changes in the body weight according to feeding duration of mice in a normal diet group (ND), a high-fat diet group (HFD), a *Platycodon grandiflorum* extract prepared by a conventional extraction method-fed group (PGE1), and a *Platycodon grandiflorum* extract of the present invention-fed group (PGE2), measured every two weeks for 12 weeks.

As a result, as shown in FIG. 8, the high-fat diet group (HFD) showed a significant increase in body weight over time compared to the normal diet group (ND), whereas the *Platycodon grandiflorum* extract prepared by a conventional extraction method-fed group (PGE1) was significantly decreased in body weight compared to the high-fat diet group. Interestingly, the *Platycodon grandiflorum* extract prepared by the extraction method of the present invention-fed group (PGE2) was continuously decreased in body weight at a level similar to that of the normal diet group during the 12-week feeding. Consequently, it can be seen that the *Platycodon grandiflorum* extract of the present invention shows an excellent effect of inhibiting an increase in body weight compared to the conventional *Platycodon grandiflorum* extract.

5-3. Comparative Analysis of Organ Weights

To compare the effect of each of the *Platycodon grandiflorum* extract of the present invention (PEG2) and the *Platycodon grandiflorum* extract prepared by a conventional extraction method (PEG1) on organ weights, by the method described in Example 2-2, liver, kidney and muscle tissues were collected from the mice of each group after the 12-week feeding according to the method described in Example 5-2, and then the weights were expressed as weight per 100 g body weight for comparison.

Figure 9:
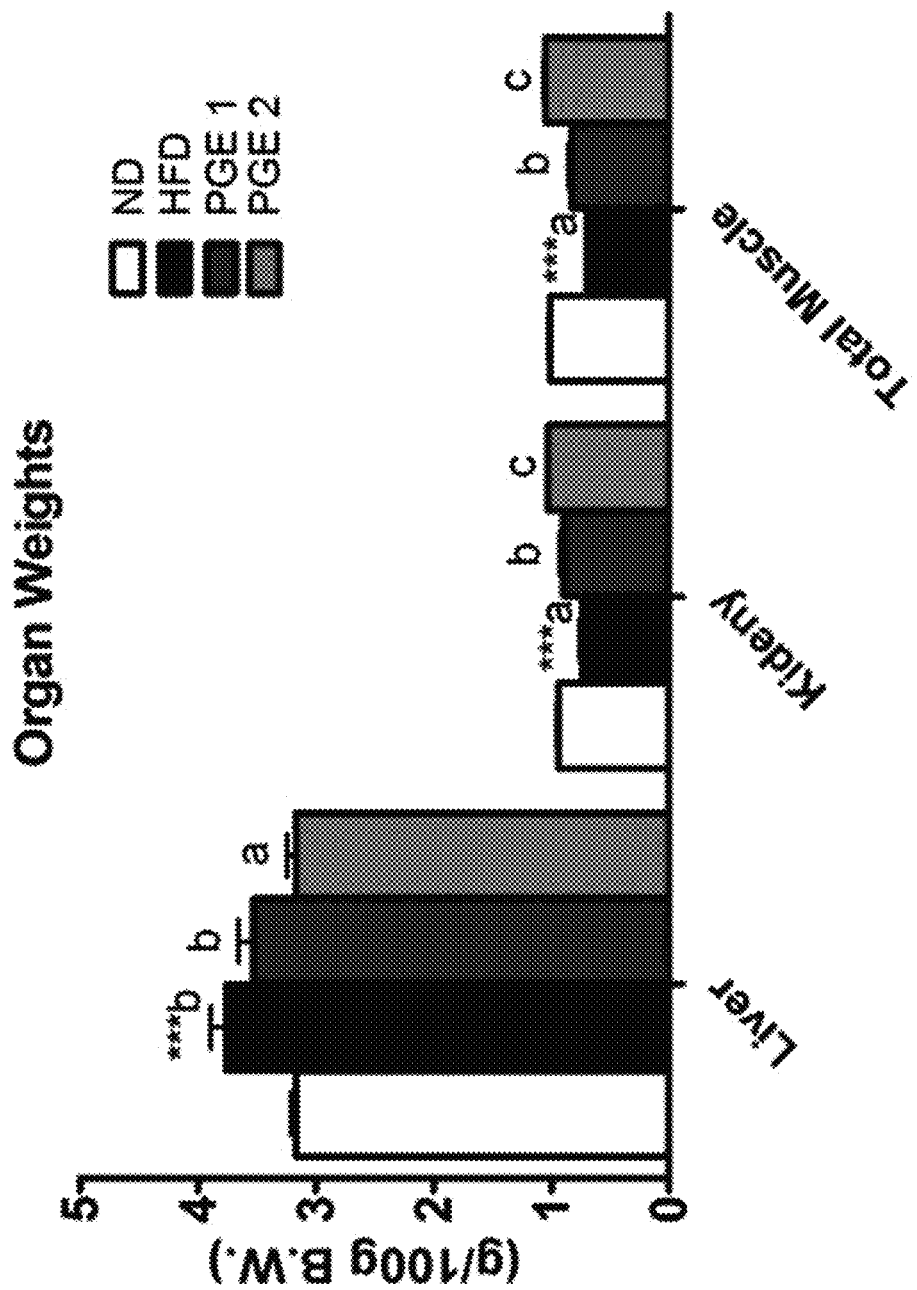
FIG. 9 shows weights of the liver, kidney and total muscle extracted from mice in a normal diet group (ND), a high-fat diet group (HFD), a *Platycodon grandiflorum* extract prepared by a conventional extraction method-fed group (PGE1), and a *Platycodon grandiflorum* extract of the present invention-fed group (PGE2), measured after 12 weeks of feeding and expressed as weight per 100 g body weight.

As a result, as shown in FIG. 9, the weight of the liver tissue was significantly increased in the high-fat diet group (HFD) compared to the normal diet group, whereas there was no significant difference in the liver weight between the *Platycodon grandiflorum* extract prepared by a conventional extraction method-fed group (PGE1) and the high-fat diet group. On the other hand, the *Platycodon grandiflorum* extract of the present invention-fed group (PGE2) showed a liver weight at a level similar to that of the normal diet group. In addition, the high-fat diet group (HFD) showed significant decreases in kidney and total muscle weights, and the *Platycodon grandiflorum* extract prepared by a conventional extraction method-fed group (PGE1) showed slight increases in these weights. However, the *Platycodon grandiflorum* extract of the present invention-fed group (PGE2) showed significant increases in kidney and total muscle weights to levels similar to those of the normal group, compared to the PGE1 group. Consequently, it can be seen that the *Platycodon grandiflorum* extract of the present invention is highly effective in inhibiting an increase in liver weight and decreases in kidney and muscle weights, compared to the conventional *Platycodon grandiflorum* extract.

5-4. Comparative Analysis of Adipose Tissue Weights

In addition to the results shown in Examples 5-2 and 5-3, to analyze changes in adipose tissue weights, epididymal WAT, perirenal WAT, retroperitoneal WAT, mesenteric WAT, visceral WAT, subcutaneous WAT, and interscapular WAT were extracted by the method described in Example 2-3 from the mice of each group after the 12-week feeding according to the method described in Example 5-2, and then the weight of each tissue and a total white fat mass were measured and expressed as weight per 100 g body weight for comparison.

Figure 10:
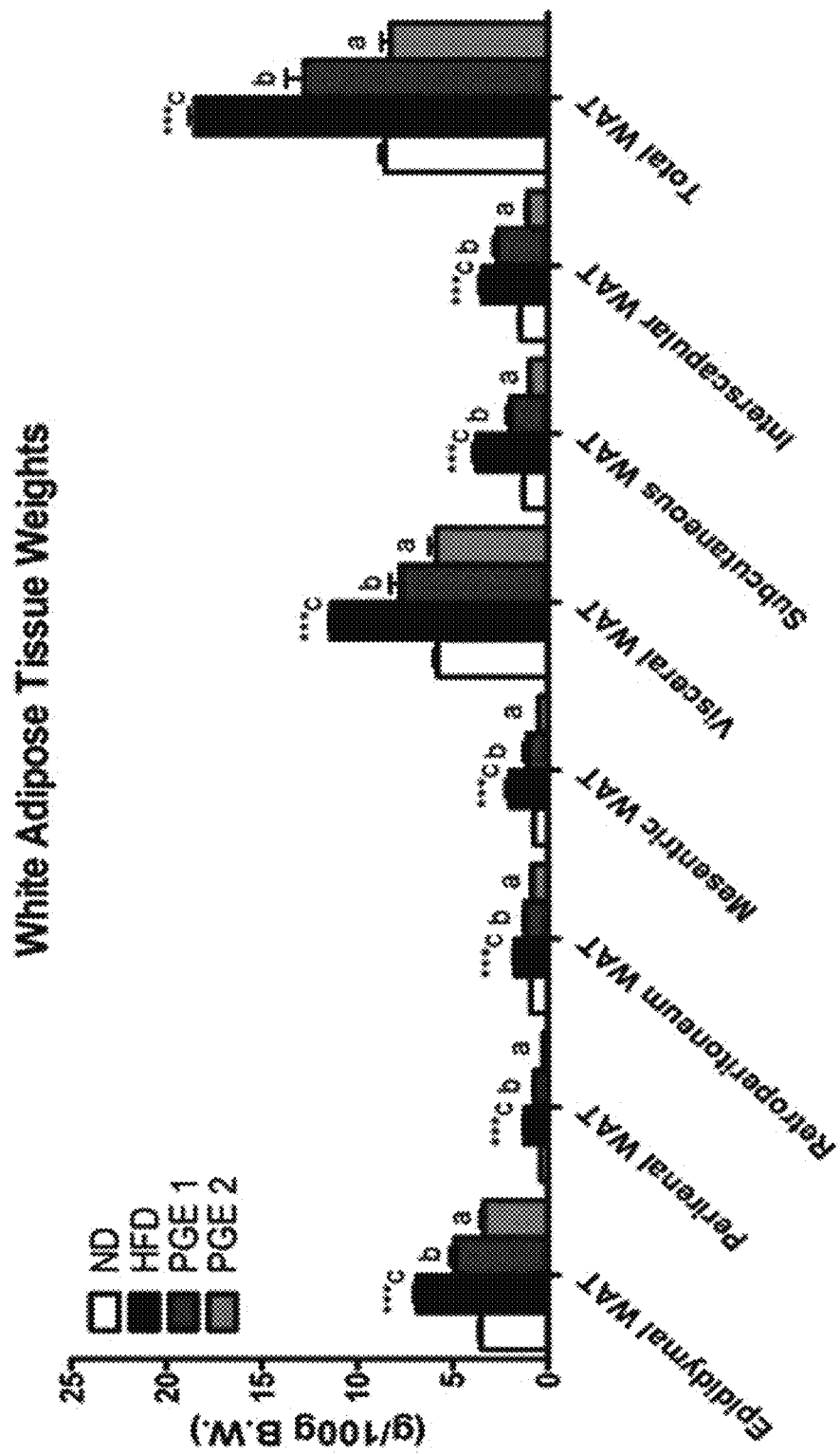
FIG. 10 shows weights of epididymal WAT, perirenal WAT, retroperitoneal WAT, mesenteric WAT, visceral WAT, subcutaneous WAT, interscapular WAT, and total WAT extracted from mice in a normal diet group (ND), a high-fat diet group (HFD), a *Platycodon grandiflorum* extract prepared by a conventional extraction method-fed group (PGE1), and a *Platycodon grandiflorum* extract of the present invention-fed group (PGE2), measured after 12 weeks of feeding and expressed as weight per 100 g body weight.

As a result, as shown in FIG. 10, the high-fat diet group (HFD) showed significant increases in the weights of all the white adipose tissue samples, whereas both of the *Platycodon grandiflorum* extract-fed groups (PGE1 and PGE2) showed significant decreases in the weights of all adipose tissue. Furthermore, the *Platycodon grandiflorum* extract of the present invention-fed group (PGE2) was highly effective in decreasing the weights of all the white adipose tissue samples compared to the *Platycodon grandiflorum* extract prepared by a conventional extraction method-fed group (PGE1), and particularly, the *Platycodon grandiflorum* extract of the present invention-fed group (PGE2) showed decreases in the total visceral WAT, the subcutaneous WAT, and the interscapular WAT to levels similar to those of the normal diet group. Consequently, it was confirmed that the *Platycodon grandiflorum* extract of the present invention-fed group has an excellent anti-obesity effect because not only body weight was decreased but also fat mass was decreased to normal group levels compared to the group fed the conventional *Platycodon grandiflorum* extract.

Example 6. Comparative Analysis of Effects of *Platycodon grandiflorum* Extract on Changes in Blood Lipids According to Extraction Method From the result obtained in Example 5, it was confirmed that the *Platycodon grandiflorum* extract of the present invention has an excellent inhibitory effect on increases in body weight and body fat compared to the *Platycodon grandiflorum* extract prepared by a conventional extraction method, and then its effect on blood lipid content was to be analyzed for comparison.

To this end, first, the mice of each group, after the 12-week feeding by the method described in Example 5-2, were fasted for 12 hours and then primary anesthetization by inhalation of isoflurane (Baxter, USA) was performed, and then fasting blood was taken from the inferior vena cava to measure contents of total cholesterol (Total-C), triglyceride (TG), free fatty acid (FFA), HDL-C, and nonHDL-cholesterol (nonHDL-C) in the plasma. The content of each lipid was measured by the following method.

Quantitation of the plasma total cholesterol was carried out with a reagent for detection (a kit produced by Asan Pharm. Co., Ltd.). Since plasma cholesterol is present in two types such as cholesteryl ester (CE) and free cholesterol, to quantify both, cholesterol esterase was used to convert CE into fatty acids and free cholesterol. The converted free cholesterol was converted into $H_2O_2$ and $\Delta^4$-cholestenone using cholesterol oxidase, and then $H_2O_2$ was stained red with a mixture of peroxidase, phenol and 4-amino-antiptrine to determine an optical density at 500 nm and compare the optical density with that of a cholesterol standard solution (300 mg/dL) for quantitation.

Plasma TG was detected using a reagent for TG detection (a kit produced by Asan Pharm. Co., Ltd.). The plasma TG was decomposed into glycerol and fatty acids using lipoprotein lipase (LPL), and then the glycerol formed L-α-glycerophosphate by the action of ATP and glycerol kinase (GK), and produced $H_2O_2$ by the reaction with $O_2$ and glycerophosphooxidase (GPO). The $H_2O_2$ was stained red with the treatment of peroxidase and 4-amino-antipyrin to determine an optical density at 550 nm, and compare the optical density with that of glycerol standard curve for quantitation.

Plasma free fatty acids were detected using a reagent for free fatty acid detection (non-esterified fatty acid, NEFA kit, Wako, Osaka, Japan). First, Acyl-CoA, AMP, and pyrophosphoric acid were produced by the action of acyl coenzyme A synthetase on the plasma free fatty acids, and then 2,3-Trans-enoyl-CoA and hydrogen peroxide were produced by the addition of acyl coenzyme A oxidase. The hydrogen peroxide was stained red with the treatment of peroxidase, 4-amino-antipyrine and N-ethyl-N-(2-hydroxy-3-sulfopropyl)-m-toluidine to determine an optical density at 555 nm and compare the optical density with that of a free fatty acid standard curve for quantitation.

Plasma HDL-C quantitation was carried out using a reagent for HDL-C detection (a kit produced by Asan Pharm. Co., Ltd., Seoul, Korea). 100 μl of plasma was taken and treated with 500 μg of sodium phosphotungstate and 1 mg of magnesium chloride, resulting in the precipitation of LDL and VLDL which including apo B among lipoproteins due to the action of phosphotungstate and magnesium cations. The resulting product was centrifuged to obtain a supernatant, and then HDL remaining in the supernatant was stained by the method used for total cholesterol to determine an optical density at 500 nm and compare the optical density with that of a cholesterol standard solution (50 mg/dL) for quantitation.

Finally, a nonHDL-cholesterol concentration was calculated by excluding a HDL-cholesterol concentration from the total cholesterol concentration.

Figure 11:
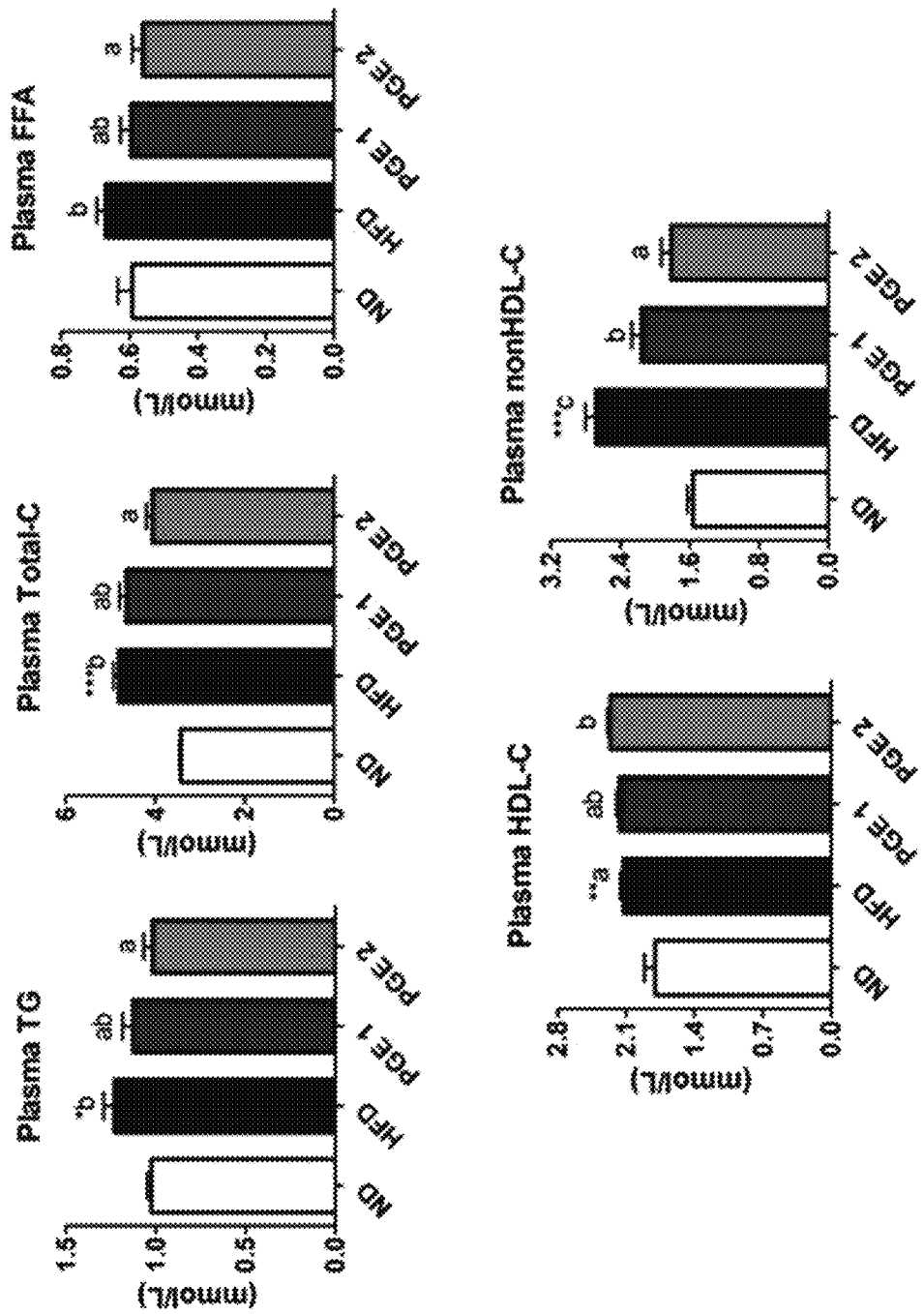
FIG. 11 shows total cholesterol (Total-C), triglyceride (TG), free fatty acid (FFA), HDL-cholesterol (HDL-C), and non HDL-cholesterol (non HDL-C) contents in plasma, measured from blood taken after 12-hour fasting of mice in a normal diet group (ND), a high-fat diet group (HFD), a *Platycodon grandiflorum* extract prepared by a conventional extraction method-fed group (PGE1), and a *Platycodon grandiflorum* extract of the present invention-fed group (PGE2), a measured after 12 weeks of feeding.

As a result of measuring the contents of various lipids in the plasma according to the above-described methods, as shown in FIG. 11, the high-fat diet group (HFD) showed increases in all of the five lipid levels compared to the normal diet group (ND). The *Platycodon grandiflorum* extract prepared by a conventional extraction method-fed group (PGE1) showed slight decreases in the TG, Total-C and FFA levels, but no significant difference compared to the high-fat diet group. Compared to the high-fat diet group, the *Platycodon grandiflorum* extract prepared by a conventional extraction method-fed group (PGE1) also showed a similar HDL-C level and only showed a significant decrease in the nonHDL-C level. On the other hand, the *Platycodon grandiflorum* extract of the present invention-fed group (PGE2) showed a decrease in TG and Total-C to levels similar to those of the normal diet group, and also showed a decrease in free fatty acid level. In addition, the *Platycodon grandiflorum* extract of the present invention-fed group (PGE2) showed an increase in the HDL-C level compared to the high-fat diet group and showed a significantly decrease in the nonHDL-C level, which was similar to that of the normal diet group. Consequently, it can be seen that the *Platycodon grandiflorum* extract of the present invention with an improved anti-obesity effect showed similar plasma lipid levels to the normal diet group, and thus had an excellent anti-obesity effect.

Example 7. Comparative Analysis of Effect of *Platycodon grandiflorum* Extract on Blood Glucose Control According to Extraction Method 7-1. Comparative Analysis of Fasting Blood Glucose and Insulin Resistance Levels For comparative analysis of the effect of each of the *Platycodon grandiflorum* extract of the present invention (PGE2) and the *Platycodon grandiflorum* extract (PGE1) prepared by a conventional extraction method on blood glucose control, first, the mice of each group fasted for 12 hours every two weeks during the 12-week feeding according to the method described in Example 5-2, and then blood was taken from the tail to determine fasting blood glucose.

Figure 12:
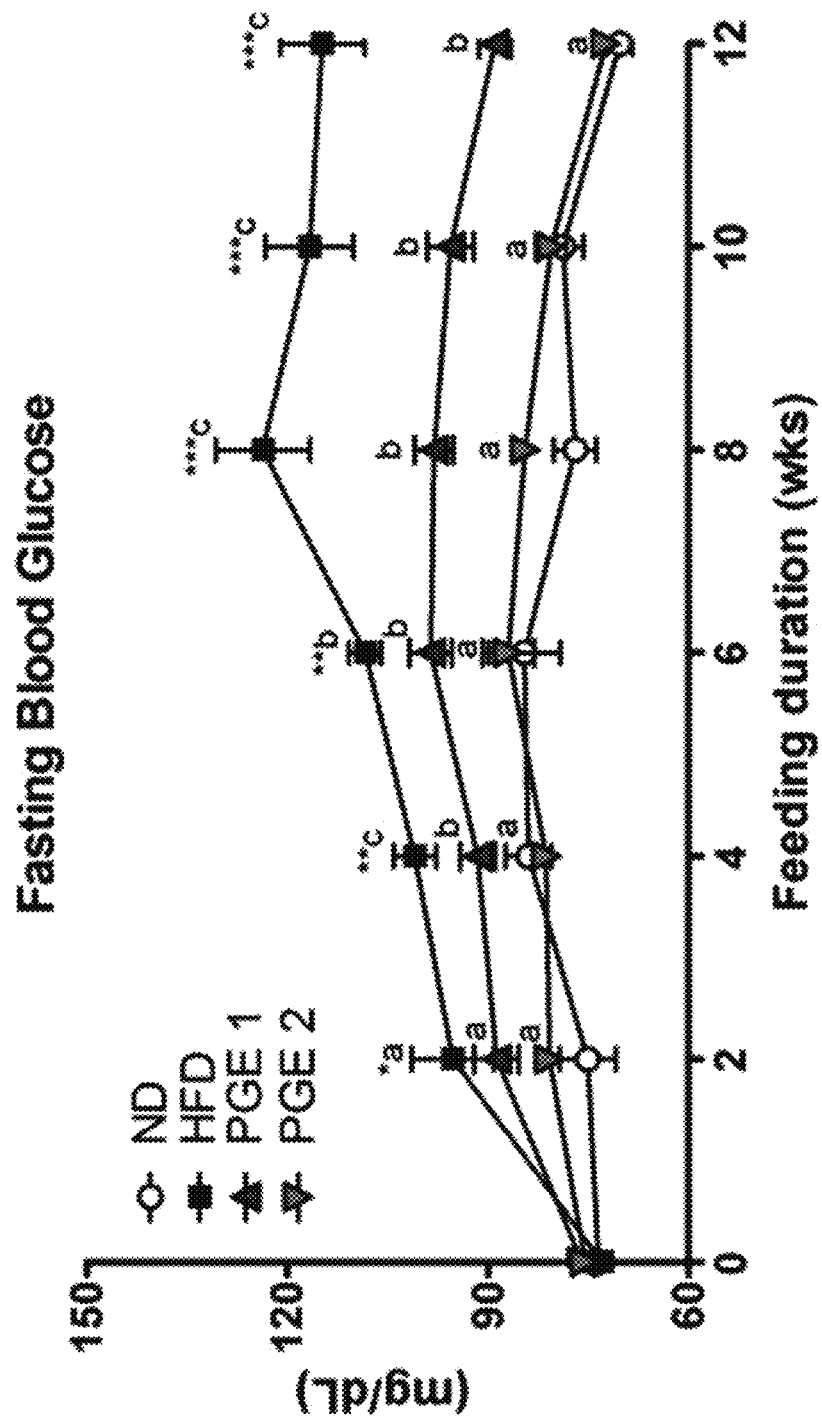
FIG. 12 shows changes in the blood glucose level according to feeding duration by measuring fasting blood glucose of mice in a normal diet group (ND), a high-fat diet group (HFD), a *Platycodon grandiflorum* extract prepared by a conventional extraction method-fed group (PGE1), and a *Platycodon grandiflorum* extract of the present invention-fed group (PGE2) every two weeks for 12 weeks.

As a result, as shown in FIG. 12, the high-fat diet group (HFD) maintained a significant blood glucose increase compared to the normal diet group (ND) from the second week of the experiment, and showed a maximum level on the 8$^{th}$ week. The *Platycodon grandiflorum* extract prepared by a conventional extraction method-fed group (PGE1) showed significantly lower blood glucose levels than the high-fat diet group from the 4$^{th}$ week, and the *Platycodon grandiflorum* extract of the present invention-fed group (PGE2) showed blood glucose levels similar to those the normal diet group throughout the 12-week feeding duration. Consequently, it was confirmed that the *Platycodon grandiflorum* extract of the present invention has an excellent effect in reducing blood glucose compared to the *Platycodon grandiflorum* extract prepared by a conventional extraction method.

Figure 13:
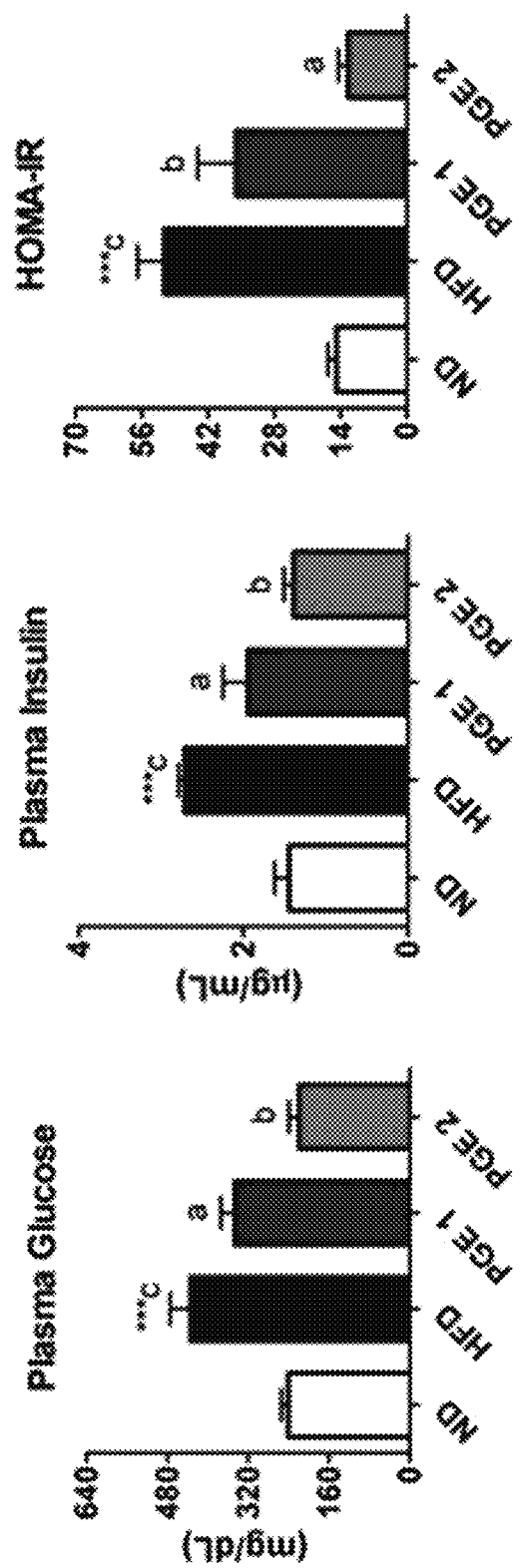
FIG. 13 shows plasma glucose and insulin contents and HOMA-IR levels of mice in a normal diet group (ND), a high-fat diet group (HFD), a *Platycodon grandiflorum* extract prepared by a conventional extraction method-fed group (PGE1), and a *Platycodon grandiflorum* extract of the present invention-fed group (PGE2), measured after 12 weeks of feeding.

Further, as a result of measuring HOMA-IR, which is an indicator that represents a plasma glucose concentration, an insulin concentration and insulin resistance, as shown in FIG. 13, the *Platycodon grandiflorum* extract of the present invention-fed group (PGE2) showed plasma glucose, insulin and HOMA-IR levels similar to those of the normal diet group, indicating that these levels are lower than those of the *Platycodon grandiflorum* extract prepared by a conventional extraction method-fed group (PGE1). Consequently, it can be seen that the *Platycodon grandiflorum* extract according to the present invention also had an excellent effect in improving insulin resistance compared to the *Platycodon grandiflorum* extract prepared by a conventional extraction method.

7-2. Measurement of Plasma Adipokine Contents

In addition to the above result, plasma adipokine contents were measured for comparison. Adipokines such as leptin, resistin and tumor necrosis factor-α (TNF-α) have a critical effect on the control of lipid metabolism, energy homeostasis and insulin sensitivity and the onset of obesity-related metabolic diseases. To measure the plasma adipokine levels, a Multiplex detection kit (Bio-Rad, USA) and a Luminex 200 Labmap system (Bio-Rad, USA) were used, and data analysis was carried out using Bio-Plex manager software version 5.0 (Bio-Rad).

Figure 14:
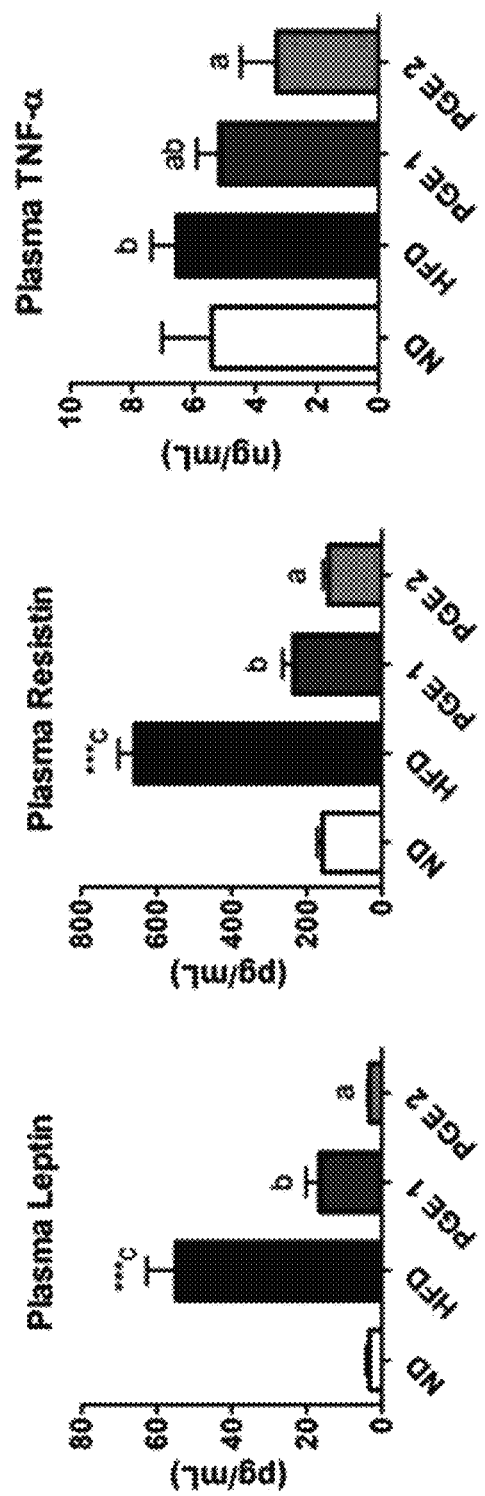
FIG. 14 shows the levels of plasma adipokines such as leptin, resistin and tumor necrosis factor-α (TNF-α) contents of mice in a normal diet group (ND), a high-fat diet group (HFD), a *Platycodon grandiflorum* extract prepared by a conventional extraction method-fed group (PGE1), and a *Platycodon grandiflorum* extract of the present invention-fed group (PGE2), measured after 12 weeks of feeding.

As a result of the measurement, as shown in FIG. 14, the high-fat diet group (HFD) showed a significant increase in adipokine content, whereas the *Platycodon grandiflorum* extract prepared by a conventional extraction method-fed group (PGE1) showed significant decreases in leptin and resistin levels, and no significant difference in the TNF-α level, compared to the high-fat diet group. On the other hand, the *Platycodon grandiflorum* extract of the present invention-fed group (PGE2) showed leptin, resistin and TNF-α levels similar to those of the normal diet group. Consequently, it can be seen that the *Platycodon grandiflorum* extract of the present invention had a more excellent effect of inhibiting an increase in plasma adipokine levels than the *Platycodon grandiflorum* extract prepared by a conventional extraction method.

It was confirmed that a *Platycodon grandiflorum* extract of the present invention has an effect of normalizing body weight and fat mass by suppressing their increases due to a high-fat diet. And it also suppressing an increase in fasting blood glucose, while increasing in energy expenditure in DIO mouse model. In addition, compared to a *Platycodon grandiflorum* extract prepared by a conventional extraction method, the *Platycodon grandiflorum* extract of the present invention was identified to have an excellent anti-obesity effect through experiments to show that it has considerably excellent effects of inhibiting increases in body weight and fat mass, an increase in fasting blood glucose, and increases in blood lipid and adipokine contents. The *Platycodon grandiflorum* extract prepared by an extraction method according to the present invention is expected to be useful for preventing or treating obesity and obesity-induced complications that can be caused by fat mass increment.

It would be understood by those of ordinary skill in the art that the above description of the present invention is exemplary, and the exemplary embodiments disclosed herein can be easily modified into other specific forms without departing from the technical spirit or essential features of the present invention. Therefore, the exemplary embodiments described above should be interpreted as illustrative and not limited in any aspect.

What is claimed is:

1. A method for preventing, improving, or treating obesity, comprising: administering a composition comprising a *Platycodon grandiflorum* extract as an active ingredient to a subject in need thereof, and thereby normalizing or decreasing body weight and fat mass, wherein the *Platycodon grandiflorum* extract is prepared by the method comprising: (a) extracting *Platycodon grandiflorum* at 45 to 55° C. during 5 to 7 hours by adding an ethanol; and (b) concentrating the resulting extract under reduced pressure and lyophilizing the extract, wherein the *Platycodon grandiflorum* extract comprises at least one active ingredient selected from the group consisting of 3"-Oacetylplatyconic acid A, 3"-O-acetylplatycodin D, and platycodin A, and wherein the content of 3"-O-acetylplatyconic acid A, 3"-O-acetylplatycodin D, or platycodin A in the *Platycodon grandiflorum* extract is more than the content of platycodin D.

2. The method of claim 1, wherein the *Platycodon grandiflorum* extract is contained at 3 to 10 wt % with respect to the total weight of the composition.

3. The method of claim 1, wherein the *Platycodon grandiflorum* extract is prepared by the method comprising the following steps:

(a) extracting *Platycodon grandiflorum* by adding 30 L of 70% ethanol for every 3 kg of *Platycodon grandiflorum* for 6 hours at 50° C.;

(b) concentrating the extract under reduced pressure at 50° C.; and (c) lyophilizing the extract.

4. The method of claim 1, wherein the *Platycodon grandiflorum* extract further comprises at least one active ingredient selected from the group consisting of deapioplatycoside E,
platycoside E,
deapioplatycodin D3,
platyconic acid B Lactone,
polygalacin D3,
platycoinc acid A,
3"-O-acetylplatycodin D2,
polygalacin D2,
polygalacin D,
platycodin V,
2"-O-acetylpolygalacin D2 and
2"-O-acetylpolygalacin D.

5. The method of claim 1, wherein the composition inhibits increases in body weight and fat mass.

6. The method of claim 1, wherein the composition inhibits an increase in blood glucose.

7. The method of claim 1, wherein the composition inhibits a decrease in energy expenditure.

8. The method of claim 1, wherein the composition inhibits an increase in blood lipid content.

9. The method of claim 1, wherein the composition inhibits an increase in blood adipokine content.

* * * * *